United States Patent
Tabibzadeh et al.

(10) Patent No.: US 6,649,588 B1
(45) Date of Patent: Nov. 18, 2003

(54) INHIBITION OF TGF-β AND USES THEREOF

(75) Inventors: Siamak Tabibzadeh, Albertson, NY (US); James M. Mason, Bethpage, NY (US)

(73) Assignee: North Shore - Long Island Jewish Research Institute, Manhasset, NY (US)

( * ) Notice: Subject to any disclaimer, the term of this patent is extended or adjusted under 35 U.S.C. 154(b) by 0 days.

(21) Appl. No.: 09/679,971

(22) Filed: Oct. 5, 2000

(51) Int. Cl.[7] .................. A61K 38/00; A01N 25/00; C07K 17/00
(52) U.S. Cl. ................ 514/2; 514/21; 514/899; 530/350
(58) Field of Search .................. 514/2, 44, 21, 514/899; 530/350

(56) References Cited

U.S. PATENT DOCUMENTS

| | | | |
|---|---|---|---|
| 5,821,227 A | 10/1998 | Dennis et al. | |
| 5,916,751 A | 6/1999 | Tabibzadeh et al. | |

OTHER PUBLICATIONS

Crystal, transfer of genes to humans: early lessons and obstacles to success, 1995, SCIENCE, vol. 270, pp. 404–409.*

Giorgio Palu et al. In pursuit of new developments for gene therapy of human diseases Journal of Biotechnolgy 68 1999 1–13.*

Tabibzadeh, S., et al., Dysregulated Expression of ebaf, a Novel Molecular Defect in the Endometria of Patients with Infertility, The Journal of Clinical Endocrinology & Metabolism, 2000, vol. 85, No. 7, pp. 2526–2536.

* cited by examiner

*Primary Examiner*—Remy Yucel
*Assistant Examiner*—Konstantina Katcheves
(74) *Attorney, Agent, or Firm*—Amster, Rothstein & Ebenstein LLP

(57) ABSTRACT

The present invention provides a method for inhibiting activity of TGF-β, comprising contacting tissue expressing TGF-β with an amount of ebaf or an ebaf analogue. The present invention further provides a method for treating a condition associated with overactivity of TGF-β, particularly fibrosis, a defect in cell proliferation, or a coagulation defect. The present invention also provides a method for inhibiting activity of TGF-β, comprising contacting tissue expressing TGF-β with a modulator of ebaf expression, or a modulator of expression of an ebaf analogue. The present invention is further directed to a method for treating fibrosis in a subject in need of treatment, comprising administering to the subject an amount of ebaf or an ebaf analogue effective to treat the fibrosis. Finally, the present invention provides a method for treating a defect in cell proliferation in a subject in need of treatment, comprising administering to the subject an amount of ebaf or an ebaf analogue effective to treat the defect in cell proliferation.

17 Claims, 13 Drawing Sheets cDNA sequence

```
AATTCGGCACGAGCCCCACTCTGCCTCCTGCTCCCCCAGGGCAGCACCATGTGG
CCCCTGTGGCTCTGCTGGGCACTCTGGGTGCTGCCCCTGGCTGGCCCCGGGGCG
GCCCTGACCGAGGAGCAGCTCCTGGGCAGCCTGCTGCGGCAGCTGCAGCTCAG
CGAGGTGCCCGTACTGGACAGGGCCGACATGGAGAAGCTGGTCATCCCCGCCC
ACGTGAGGGCCCAGTATGTAGTCCTGCTGCGGCGCAGCCACGGGGACCGCTCC
CGCGGAAAGAGGTTCAGCCAGAGCTTCCGAGAGGTGGCCGGCAGGTTCCTGGC
GTCGGAGGCCAGCACACACCTGCTGGTGTTCGGCATGGAGCAGCGGCTGCCGC
CCAACAGCGAGCTGGTGCAGGCCGTGCTGCGGCTCTTCCAGGAGCCGGTCCCC
AAGGCCGCGCTGCACAGGCACGGGCGGCTGTCCCCGCGCAGCGCCCAGGCCC
GGGTGACCGTCGAGTGGCTGCGCGTCCGCGACGACGGCTCCAACCGCACCTCC
CTCATCGACTCCAGGCTGGTGTCCGTCCACGAGAGCGGCTGGAAGGCCTTCGA
CGTGACCGAGGCCGTGAACTTCTGGCAGCAGCTGAGCCGGCCCCGGCAGCCGC
TGCTGCTACAGGTGTCGGTGCAGAGGGAGCATCTGGGCCCGCTGGCGTCCGGC
GCCCACAAGCTGGTCCGCTTTGCCTCGCAGGGGGCGCCAGCCGGGCTTGGGGA
GCCCCAGCTGGAGCTGCACACCCTGGACCTCAGGGACTATGGAGCTCAGGGCG
ACTGTGACCCTGAAGCACCAATGACCGAGGGCACCCGCTGCTGCCGCCAGGAG
ATGTACATTGACCTGCAGGGGATGAAGTGGGCCAAGAACTGGGTGCTGGAGCC
CCCGGGCTTCCTGGCTTACGAGTGTGTGGGCACCTGCCAGCAGCCCCCGGAGG
CCCTGGCCTTCAATTGGCCATTTCTGGGGCCGCGACAGTGTATCGCCTCGGAGA
CTGCCTCGCTGCCCATGATCGTCAGCATCAAGGAGGGAGGCAGGACCAGGCCC
CAGGTGGTCAGCCTGCCCAACATGAGGGTGCAGAAGTGCAGCTGTGCCTCGGA
TGGGGCGCTCGTGCCAAGGAGGCTCCAGCCATAGGCGCCTGGTGTA
```

Amino Acid Sequence

```
MWPLWLCWALWVLPLAGPGAALTEEQLLGSLLRQLQLSEVPVLDRADMEKLVIPAHVRAQYVVLLRRSHGD
RSRGKRFSQSFREVAGRFLASEASTHLLVFGMEQRLPPNSELVQAVLRLFQEPVPKAALHRHGRLSPRSAQ
ARVTVEWLRVRDDGSNRTSLIDSRLVSVHESGWKAFDVTEAVNFWQQLSRPRQPLLLQVSVQREHLGPLAS
GAHKLVRFASQGAPAGLGEPQLELHTLDLRDYGAQGDCDPEAPMTEGTRCCRQEMYIDLQGMKWAKNWVLE
PPGFLAYECVGTCQQPPEALAFNWPFLGPRQCIASETASLPMIVSIKEGGRTRPQVVSLPNMRVQKCSCAS
DGALVPRRLQP
```

FIG. 2

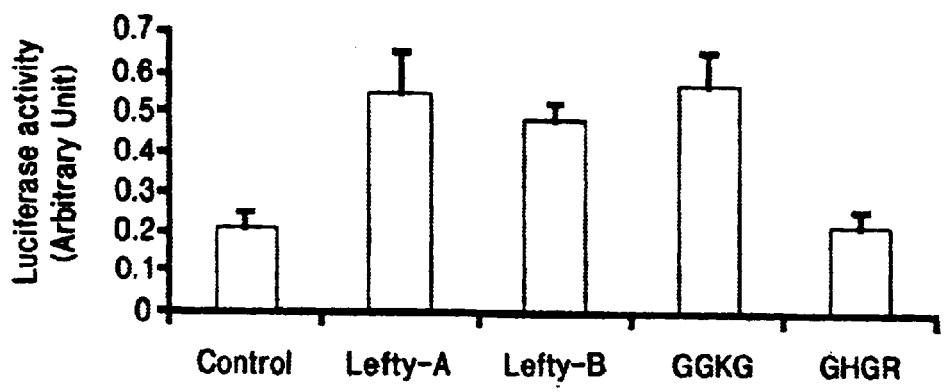
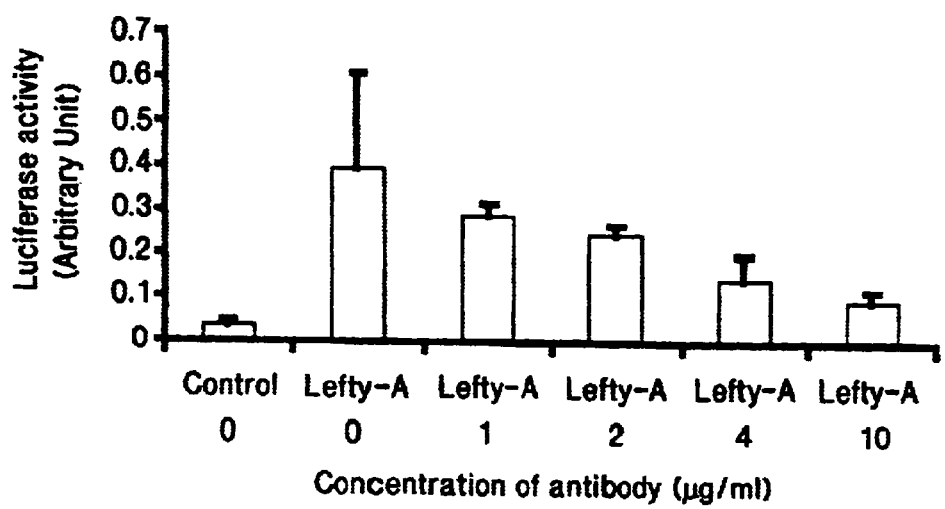
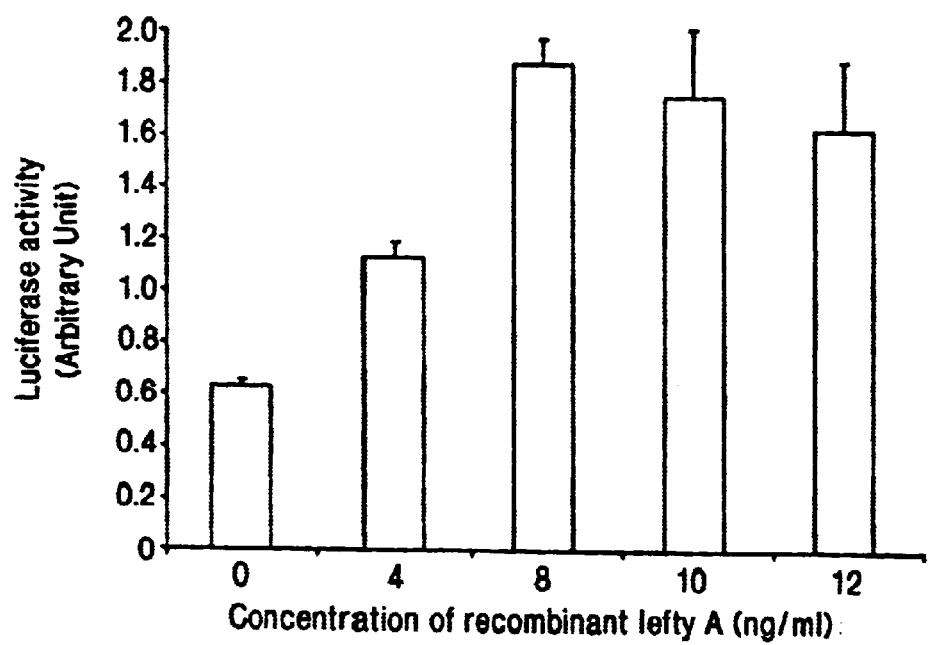
FIG. 10

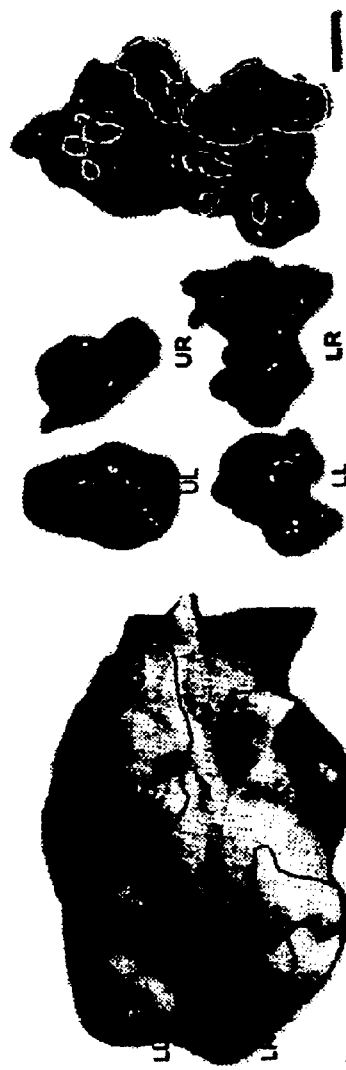
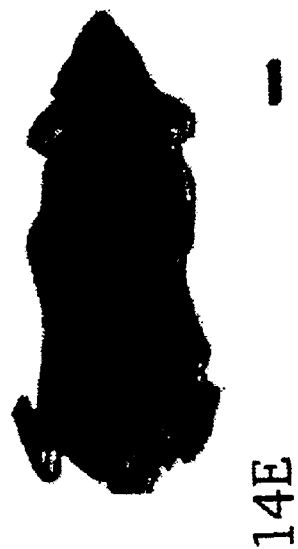
FIG. 14A  FIG. 14B
FIG. 14C  FIG. 14D
FIG. 14E  FIG. 14F

SEQUENCE LISTING

<160> NUMBER OF SEQ ID NOS: 4

<210> SEQ ID NO 1
<211> LENGTH: 1161
<212> TYPE: DNA
<213> ORGANISM: Homo sapiens

<400> SEQUENCE: 1

```
aattcggcac gagccccact ctgcctcctg ctcccccagg gcagcaccat gtggcccctg      60
tggctctgct gggcactctg ggtgctgccc ctggctggcc ccggggcggc cctgaccgag     120
gagcagctcc tgggcagcct gctgcggcag ctgcagctca gcgaggtgcc cgtactggac     180
agggccgaca tggagaagct ggtcatcccc gcccacgtga gggcccagta tgtagtcctg     240
ctgcggcgca gccacgggga ccgctcccgc ggaaagaggt tcagccagag cttccgagag     300
gtggccggca ggttcctggc gtcggaggcc agcacacacc tgctggtgtt cggcatggag     360
cagcggctgc cgcccaacag cgagctggtg caggccgtgc tgcggctctt ccaggagccg     420
gtccccaagg ccgcgctgca caggcacggg cggctgtccc cgcgcagcgc ccaggcccgg     480
gtgaccgtcg agtggctgcg cgtccgcgac gacggctcca accgcacctc cctcatcgac     540
tccaggctgg tgtccgtcca cgagagcggc tggaaggcct tcgacgtgac cgaggccgtg     600
aacttctggc agcagctgag ccggcccgg cagccgctgc tgctacaggt gtcggtgcag     660
agggagcatc tgggcccgct ggcgtccggc gcccacaagc tggtccgctt tgcctcgcag     720
ggggcgccag ccgggcttgg ggagcccag ctggagctgc acaccctgga cctcagggac     780
tatggagctc agggcgactg tgaccctgaa gcaccaatga ccgagggcac ccgctgctgc     840
```

-continued

```
cgccaggaga tgtacattga cctgcagggg atgaagtggg ccaagaactg ggtgctggag      900
cccccgggct tcctggctta cgagtgtgtg ggcacctgcc agcagccccc ggaggccctg      960
gccttcaatt ggccatttct ggggccgcga cagtgtatcg cctcggagac tgcctcgctg     1020
cccatgatcg tcagcatcaa ggagggaggc aggaccaggc cccaggtggt cagcctgccc     1080
aacatgaggg tgcagaagtg cagctgtgcc tcggatgggg cgctcgtgcc aaggaggctc     1140
cagccatagg cgcctggtgt a                                               1161
```

<210> SEQ ID NO 2
<211> LENGTH: 366
<212> TYPE: PRT
<213> ORGANISM: Homo sapiens

<400> SEQUENCE: 2

```
Met Trp Pro Leu Trp Leu Cys Trp Ala Leu Trp Val Leu Pro Leu Ala
1               5                   10                  15

Gly Pro Gly Ala Ala Leu Thr Glu Glu Gln Leu Leu Gly Ser Leu Leu
            20                  25                  30

Arg Gln Leu Gln Leu Ser Glu Val Pro Val Leu Asp Arg Ala Asp Met
        35                  40                  45

Glu Lys Leu Val Ile Pro Ala His Val Arg Ala Gln Tyr Val Val Leu
    50                  55                  60

Leu Arg Arg Ser His Gly Asp Arg Ser Arg Gly Lys Arg Phe Ser Gln
65                  70                  75                  80

Ser Phe Arg Glu Val Ala Gly Arg Phe Leu Ala Ser Glu Ala Ser Thr
                85                  90                  95

His Leu Leu Val Phe Gly Met Glu Gln Arg Leu Pro Pro Asn Ser Glu
            100                 105                 110

Leu Val Gln Ala Val Leu Arg Leu Phe Gln Glu Pro Val Pro Lys Ala
        115                 120                 125

Ala Leu His Arg His Gly Arg Leu Ser Pro Arg Ser Ala Gln Ala Arg
    130                 135                 140

Val Thr Val Glu Trp Leu Arg Val Arg Asp Asp Gly Ser Asn Arg Thr
145                 150                 155                 160

Ser Leu Ile Asp Ser Arg Leu Val Ser Val His Glu Ser Gly Trp Lys
                165                 170                 175

Ala Phe Asp Val Thr Glu Ala Val Asn Phe Trp Gln Gln Leu Ser Arg
            180                 185                 190

Pro Arg Gln Pro Leu Leu Leu Gln Val Ser Val Gln Arg Glu His Leu
        195                 200                 205

Gly Pro Leu Ala Ser Gly Ala His Lys Leu Val Arg Phe Ala Ser Gln
    210                 215                 220

Gly Ala Pro Ala Gly Leu Gly Glu Pro Gln Leu Glu Leu His Thr Leu
225                 230                 235                 240

Asp Leu Arg Asp Tyr Gly Ala Gln Gly Asp Cys Asp Pro Glu Ala Pro
                245                 250                 255

Met Thr Glu Gly Thr Arg Cys Cys Arg Gln Glu Met Tyr Ile Asp Leu
            260                 265                 270

Gln Gly Met Lys Trp Ala Lys Asn Trp Val Leu Glu Pro Pro Gly Phe
        275                 280                 285

Leu Ala Tyr Glu Cys Val Gly Thr Cys Gln Gln Pro Pro Glu Ala Leu
    290                 295                 300

Ala Phe Asn Trp Pro Phe Leu Gly Pro Arg Gln Cys Ile Ala Ser Glu
```

```
305                 310                 315                 320
Thr Ala Ser Leu Pro Met Ile Val Ser Ile Lys Glu Gly Gly Arg Thr
                325                 330                 335

Arg Pro Gln Val Val Ser Leu Pro Asn Met Arg Val Gln Lys Cys Ser
            340                 345                 350

Cys Ala Ser Asp Gly Ala Leu Val Pro Arg Arg Leu Gln Pro
        355                 360                 365

<210> SEQ ID NO 3
<211> LENGTH: 39
<212> TYPE: DNA
<213> ORGANISM: artificial sequence
<220> FEATURE:
<221> NAME/KEY: primer_bind
<222> LOCATION: (1)..(39)
<223> OTHER INFORMATION: oligonucleotide primer NS204 used as PCR primer

<400> SEQUENCE: 3
aaagatatcg catgccctct ccctccccc cccctaacg                              39

<210> SEQ ID NO 4
<211> LENGTH: 39
<212> TYPE: DNA
<213> ORGANISM: artificial sequence
<220> FEATURE:
<221> NAME/KEY: primer_bind
<222> LOCATION: (1)..(39)
<223> OTHER INFORMATION: oligonucleotide primer NS205 used as PCR primer

<400> SEQUENCE: 4
tttgatatcc tcgagttact tgtacagctc gtccatgcc                             39
```

US 6,649,588 B1

INHIBITION OF TGF-β AND USES THEREOF

STATEMENT OF GOVERNMENT INTEREST

This invention was made with government support under NIH Grant No. CA8466. As such, the United States Government has certain rights in this invention.

BACKGROUND OF THE INVENTION

Transforming growth factor-beta (TGF-β) is a pleiotropic peptide that controls proliferation and differentiation of many cell types, and modulates the coagulation process. Many cells synthesize TGF-β, and almost all of them have specific receptors for this peptide.

The activities of TGF-β are well documented. TGF-β inhibits the growth of epithelial cells (Böttinger et al., 1997; Hall et al., 1996; Kornmann, 1999; Morton and Barrack, 1995; and Mur et al., 1998), but promotes the proliferation of fibroblasts (Bettinger et al., 1996; Clark et al., 1997; and Franzen and Dahlquist, 1994) and the deposition of collagen (Bettinger et al., 1996; and Han, 1999). In particular, TGF-p has been implicated in various forms of fibrosis, including: normal wound healing and scar formation (Choi et al., 1996; Lin et al., 1995; Liu et al., 1995; Messadi, 1998; O'Kane and Ferguson, 1997; and Stelnicki et al., 1998); the formation of keloid (Lee, 1999; Tredget et al., 1998; Younai et al., 1994; and Zhang et al., 1995); radiation-induced fibrosis (Randall and Coggle, 1996); fibromatosis (Berndt et al., 1995; and Zamora et al., 1994); hypertrophic burn scars (Polo et al., 1997; and Zhang et al., 1995); pulmonary fibrosis (Khalil et al., 1996; Martinet et al., 1996; Specks et al., 1995; Vaillant et al., 1996; and Yoshida and Hayashi, 1996), including that associated with radiation (Yi et al., 1996), drugs (Coker et al., 1997; and Zhang et al., 1996), and transplantation (El-Gamel et al., 1998); the healing of the myocardial infarct (Hao et al., 1999); fibrosis associated with autoimmune disorders such as scieroderma (Querfeld et al., 1999); and sarcoidosis (Salez et al., 1998).

In view of the wide-ranging activities of TGF-β, it is clear that overactivity of TGF-β is implicated in the conditions of fibrosis, defects in cell proliferation, and coagulation defects. Thus, a factor which inhibits the activity of TGF-β would be extremely useful in treating those conditions associated with the overactivity of TGF-β. However, there are currently no known effective inhibitors of TGF-β.

Recently, a new member of the TGF-β superfamily, lefty-1, was recognized for its distinct asymmetric expression in gastrulating mouse embryos (Meno et al., 1996; and Oulad-Abdelghani et al., 1998). Lefty-A is the human homologue of lefty-1. Lefty-A is also known as endometrial bleeding associated factor (ebaf) protein, which is associated with abnormal endometrial bleeding (Kothapalli et al. (1997).

The ebaf gene is located on human chromosome 1, at band q42.1, and its nucleotide and deduced amino acid sequences are known. Ebaf is highly expressed in human endometrium prior to and during menstrual bleeding or abnormal uterine bleeding (Kothapalli et al., 1997). The ebaf gene is also expressed in certain adenocarcinomas that exhibit mucinous differentiation, including colonic, duodenal, ovarian, and testicular carcinomas (Tabibzadeh et al., 1997). The amino acid sequence of the ebaf protein shows homology with, and structural features of, members of the TGF-β superfamily (Kothapalli et al., 1997), and ebaf is also recognized as a member of the TGF-β superfamily.

In view of the similarity in the nucleotide sequences of lefty-1 and ebaf, Kosaki et al. (1999) hypothesized, and subsequently showed, that mutations in the ebaf gene are associated with left-right axis malformations in humans. During the course of this investigation, a second human gene, lefty-B, was identified. In mice, both the lefty-1 gene and the lefty-2 gene reside on chromosome 1H2. In humans, both the lefty-A (ebaf) gene and the lefty-B gene map to human syntenic region 1q42, and are separated from each other by 50 kb. The nucleotide sequences of lefty-A (ebaf) and lefty-B are 97% identical, so these proteins are more closely related to each other than to either of the mouse homologues.

Human ebaf proteins are derived from a precursor with an approximate molecular weight of 42 kD. Polypeptides with approximate molecular weights of 34 kD and 28 kD are secreted by cells, along with the precursor. RGKR and RHGR are the cleavage sites, respectively, for the 34-kD and 28-kD protein forms. Lefty proteins are secreted in glycosylated form.

SUMMARY OF THE INVENTION

The present invention is based upon the discovery that ebaf inhibits activity of TGF-β. On the basis of this finding, the present invention provides a method for inhibiting activity of TGF-β, comprising contacting tissue expressing TGF-β with an amount of ebaf or an ebaf analogue effective to inhibit the activity of TGF-β.

The present invention further provides a method for treating a condition associated with overactivity of TGF-β in a subject in need of treatment, comprising contacting tissue expressing TGF-β in the subject with an amount of ebaf or an ebaf analogue effective to inhibit activity of TGF-β, thereby treating the condition.

The present invention also discloses a method for inhibiting activity of TGF-β, comprising contacting tissue expressing TGF-β with a modulator of ebaf expression, or a modulator of expression of an ebaf analogue, in an amount effective to induce or enhance expression of ebaf or the ebaf analogue, thereby inhibiting the activity of TGF-β.

The present invention is further directed to a method for treating fibrosis in a subject in need of treatment, comprising administering to the subject an amount of ebaf or an ebaf analogue effective to treat the fibrosis.

Finally, the present invention provides a method for treating a defect in cell proliferation in a subject in need of treatment, comprising administering to the subject an amount of ebaf or an ebaf analogue effective to treat the defect in cell proliferation.

Additional objects of the present invention will be apparent in view of the description which follows.

BRIEF DESCRIPTION OF THE FIGURES

FIG. 2 depicts the nucleotide sequence (SEQ ID NO:1) and corresponding amino acid sequence (SEQ ID NO:2) for ebaf.

FIG. 2 depicts the nucleotide sequence (SEQ ID NO:1) and corresponding amino acid sequence (SEQ ID NO:2) for ebaf.

FIG. 10 depicts activation of the MAPK pathway by ebaf-conditioned media. upper panel: 293 cells were transfected with the mutated GGKG (amino acid residues 74–77) and GHGR (amino acid residues 132–135) forms of ebaf. The conditioned media were used for the treatment of P19 cells, and activation of the MAPK pathway was visualized in vivo using the PathDetect™ reporting system. middle panel: Culture media of 293 cells transfected with empty pcDNA3 vector or ebaf were incubated with the indicated concentrations of anti-ebaf antibody, A351, to block the activity of ebaf in the medium. The media were used to treat the pluripotent mouse P19 embryonal carcinoma cells. Activation of the MAPK pathway was analyzed in vivo using the luciferase reporting system, as indicated in Materials and Methods. lower panel: P19 cells were incubated with the indicated concentrations of recombinant ebaf corresponding to the 28-kD form of ebaf (amino acid residues S137-P366). Activation of the MAPK pathway was visualized in vivo using the PathDetect™ reporting system, as indicated in Materials and Methods. The error bars show the standard deviation for three different experiments.

FIGS. 14A–14F illustrates the effect of ebaf on the growth of fibroblastic cells in vivo. GE+E86 cells were transduced with a retroviral vector expressing green fluorescent protein (LG) or green fluorescent protein (GFP) and ebaf (LEIG). Cells were grown in culture. After 24 h, conditioned media were tested for the presence of ebaf. Ebaf was secreted by LEIG cells, but not by LG cells. $5 \times 10^6$ LG cells (panels A–D) or LEIG cells (panels E–F) were injected subcutaneously into nu/nu mice at the upper left (UL), upper right (UR), lower left (LL), and lower right (LR) aspects of the back. Each animal also was injected intraperitoneally with $5 \times 10^6$ cells. Three weeks after injection, the animals were sacrificed. The subcutaneous tumors (marked by black lines in panels A, C, and E) were removed; these are shown in panels B, D, and F. The thoracic and abdominal organs were removed en bloc; these are shown to the right of the subcutaneous tumors in panels B, D, and F. The peritoneal tumors are marked by white lines. The volume of each subcutaneous tumor then was determined. volumes of subcutaneous tumors: panel B: UL: 3.5 cc, UR: 2 cc, LL: 2.5 cc, LR: 4 cc; panel D: UL: 2 cc, UR: 3.9 cc, LL: 1.2 cc, LR: 1.3 cc; panel F: UL: 0.6 cc, UR: 0.7 cc, LL: 0.7 cc, LR: 0.5 cc

DETAILED DESCRIPTION OF THE INVENTION

Figure 1:
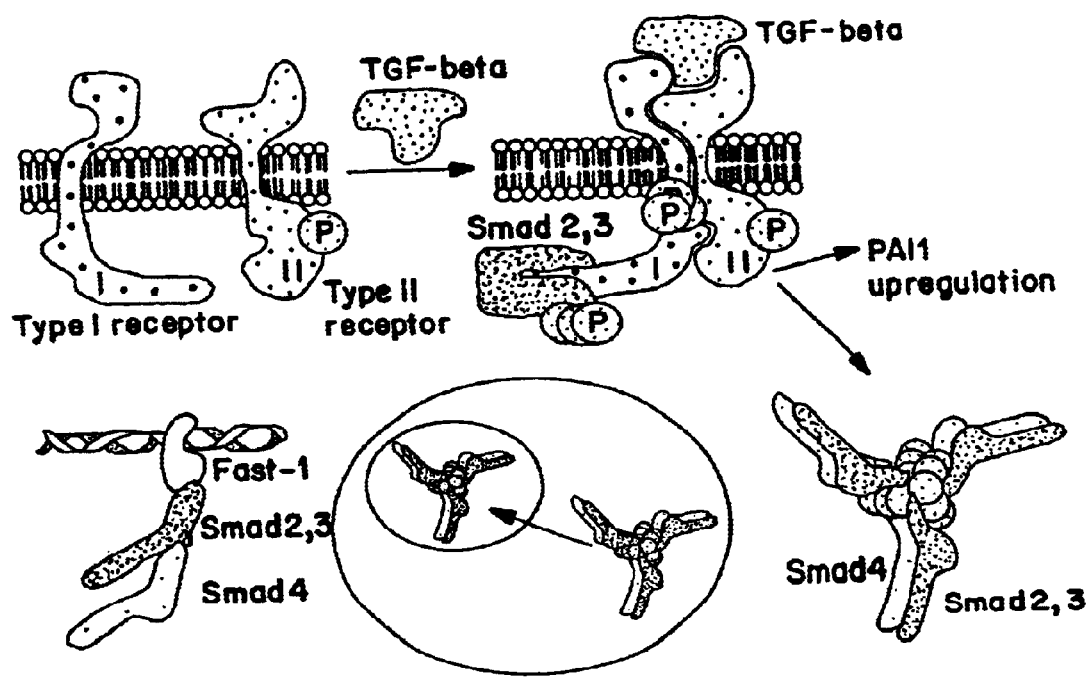
FIG. 1 provides a model for TGF-β signaling. TGF-β functions through binding to two receptors, and signals through the Smad family of transcription factors. The biological effects of the members of the TGF-β family are signaled through two classes of molecules, designated as type I and type II receptors. These are transmembrane serine-threonine kinases that share homology with each other, but have distinctive features. The dimerized ligand first binds the type II receptor; the type I receptor is subsequently recruited, leading to the formation of a heteromeric complex. Within this complex, the type II receptor, which is constitutively active, phosphorylates the type I receptor in the GS (glycine-serine rich) domain (Padgett et al., 1998).

The present invention provides a method for inhibiting TGF-β activity, comprising contacting tissue expressing TGF-β with an amount of ebaf effective to inhibit the activity of TGF-β. Unless otherwise indicated, "ebaf" includes both an ebaf (lefty-A) protein and an "ebaf analogue". As used herein, ebaf protein has the amino acid sequence set forth in FIG. 2. An "ebaf analogue" is a functional variant of the ebaf protein, having ebaf-protein biological activity, that has 80% or greater (preferably, 90% or greater) amino-acid-sequence homology with the ebaf protein, as well as a fragment of the ebaf protein having ebaf-protein biological activity. As used herein, the term "ebaf-protein biological activity" refers to protein activity which inhibits activity of TGF-β, as disclosed below. Additionally, the term "ebaf analogue", as defined herein, includes peptides related to ebaf that exert similar ebaf-protein biological activity, particularly lefty-B, lefty-1, and lefty-2 proteins, and preferably lefty-B. Ebaf may be produced synthetically or recombinantly, or may be isolated from native cells; however, it is preferably produced recombinantly, using cDNA encoding ebaf (FIG. 2), along with conventional techniques.

The method of the present invention may be used to inhibit activity of TGF-β in vitro or in vivo. As used herein, the term "inhibit activity of TGF-β" means inhibit the signaling mechanisms of TGF-β, as disclosed herein, including Smad2 phosphorylation, Smad2/4 heterodimerization, and Smad2 and Smad4 nuclear translocation, as well as associated downstream signaling. Inhibition of these signaling mechanisms by TGF-β may be detected by known procedures, including any of the methods, molecular procedures, and assays disclosed herein.

In accordance with the methods of the present invention, ebaf or an ebaf analogue may be contacted with tissue expressing TGF-β by introducing to the tissue the ebaf or ebaf analogue protein itself, or by introducing to the tissue a nucleic acid encoding ebaf or the ebaf analogue in a manner permitting expression of ebaf or ebaf analogue protein. Expression of TGF-β may be detected in tissue by detection methods readily determined from the known art, including, without limitation, immunological techniques (e.g., binding studies and Western blotting), hybridization analysis (e.g., using nucleic acid probes), fluorescence imaging techniques, and/or radiation detection.

Ebaf protein or ebaf analogue protein may be introduced to tissue expressing TGF-β in vivo in a subject by known techniques used for the introduction of proteins, including, for example, injection and transfusion. The subject is preferably a mammal (e.g., humans, domestic animals, and commercial animals), and is most preferably a human. When tissue expressing TGF-β is localized to a particular portion of the body of the subject, it may be desirable to introduce the protein directly to the tissue by injection or by some other means (e.g., by introducing ebaf or an ebaf analogue into the blood or another body fluid). The amount of ebaf protein or ebaf analogue protein to be used is an amount effective to inhibit activity of TGF-β, and may be readily determined by the skilled artisan.

In the method of the present invention, ebaf or an ebaf analogue also may be introduced to tissue expressing TGF-β by introducing into a sufficient number of cells of the tissue a nucleic acid encoding ebaf or the ebaf analogue, in a manner permitting expression of ebaf or the ebaf analogue. The nucleic acid may be introduced using conventional procedures known in the art, including, without limitation, electroporation, DEAE Dextran transfection, calcium phosphate transfection, monocationic liposome fusion, polycationic liposome fusion, protoplast fusion, creation of an in vivo electrical field, DNA-coated microprojectile bombardment, injection with recombinant replication-defective viruses, homologous recombination, gene therapy, viral vectors, and naked DNA transfer, or any combination thereof. Recombinant viral vectors suitable for gene therapy include, but are not limited to, vectors derived from the genomes of viruses such as retrovirus, HSV, adenovirus, adeno-associated virus, Semiliki Forest virus, cytomegalovirus, and vaccinia virus. The amount of ebaf protein or ebaf analogue protein to be used is an amount effective to inhibit activity of TGF-β. This amount may be readily determined by the skilled artisan.

It is also within the confines of the present invention that a nucleic acid encoding ebaf or an ebaf analogue may be introduced into suitable cells in vitro using conventional procedures. Cells expressing ebaf or the ebaf analogue then may be introduced into a subject to inhibiting activity of TGF-β in vivo. To reduce rejection, the cells are preferably removed from the subject, subjected to DNA techniques to incorporate nucleic acid encoding ebaf or the ebaf analogue, and then reintroduced into the subject.

The ability of ebaf to inhibit activity of TGF-β renders ebaf particularly useful for treating conditions associated with overactivity of TGF-β. As used herein, "overactivity of TGF-p" includes pathologic activity of TGF-β and pathologic expression of TGF-β in a particular tissue, as compared with normal activity of TGF-β and normal expression of TGF-β in the same type of tissue. It is believed that, by inhibiting activity of TGF-β, ebaf and ebaf analogues will be useful for the treatment of conditions associated with the overactivity of TGF-β. It is further believed that ebaf and ebaf analogues would be effective either alone or in combination with therapeutic agents, such as chemotherapeutic agents or antiviral agents, which are typically used in the treatment of these conditions.

Accordingly, the present invention provides a method for treating a condition associated with overactivity of TGF-β in a subject in need of treatment, comprising contacting tissue expressing TGF-β in the subject with an amount of ebaf or an ebaf analogue effective to inhibit activity of TGF-β, thereby treating the condition. As described above, the subject is preferably a mammal (e.g., humans, domestic animals, and commercial animals), and is most preferably a human.

In the treatment of a condition associated with overactivity of TGF-β, ebaf or an ebaf analogue may be contacted with tissue expressing TGF-β by introducing to the tissue the ebaf protein or ebaf analogue protein itself, in accordance with known methods, including injection, transfusion, and any methods described above. For example, when tissue expressing TGF-β is localized to a particular portion of the body of the subject, it may be desirable to introduce the protein directly to the tissue by injection or by some other means (e.g., by introducing ebaf or an ebaf analogue into the blood or another body fluid). The amount of ebaf protein or ebaf analogue protein to be used is an amount effective to inhibit activity of TGF-β, as defined above, and may be readily determined by the skilled artisan.

Alternatively, in accordance with known methods, including those described above, ebaf or an ebaf analogue may be contacted with tissue expressing TGF-β by introducing to the tissue a nucleic acid encoding ebaf or an ebaf analogue, in a manner permitting expression of ebaf protein or ebaf analogue protein. The nucleic acid may be introduced using conventional procedures known in the art, including, without limitation, electroporation, DEAE Dextran transfection, calcium phosphate transfection, monocationic liposome fusion, polycationic liposome fusion, protoplast fusion, creation of an in vivo electrical field, DNA-coated microprojectile bombardment, injection with recombinant replication-defective viruses, homologous recombination, gene therapy, viral vectors, and naked DNA transfer, or any combination thereof. Recombinant viral vectors suitable for gene therapy include, but are not limited to, vectors derived from the genomes of viruses such as retrovirus, HSV, adenovirus, adeno-associated virus, Semiliki Forest virus, cytomegalovirus, and vaccinia virus. The amount of ebaf protein or ebaf analogue protein to be used is an amount effective to inhibit activity of TGF-β, as defined above. This amount may be readily determined by the skilled artisan.

Overactivity of TGF-β may be associated with such conditions as fibrosis, defects in cell proliferation, and coagulation defects. In the method of the present invention, ebaf or an ebaf analogue may be used to treat forms of fibrosis, including, without limitation, the following: scars, particularly scars caused by burning, radiation, chemicals, or myocardial infarct; keloid; cirrhosis; Asherman's syndrome; Meigs' syndrome; muscular dystrophies, particularly Duchenne muscular dystrophy; autoimmune disorders leading to fibrosis, particularly scleroderma; post-surgical fibrosis, particularly fibrosis induced by surgery or surgical manipulation; fibrosis induced by non-surgical manipulation; and primary pulmonary fibrosis, particularly Hamman Rich Syndrome and retroperitoneal fibrosis. In accordance with the method of the present invention, ebaf or an ebaf analogue may further be used to treat defects in cell proliferation, including, without limitation, hyperplasia and neoplasia. Finally, ebaf or an ebaf analogue also may be used to treat coagulation defects, including menstrual bleeding, abnormal uterine bleeding, coagulopathies, and toxemia of pregnancy.

The present invention further provides a method for inhibiting activity of TGF-β in tissue, comprising contacting tissue expressing TGF-β with a modulator of ebaf expression, or a modulator of expression of an ebaf analogue, in an amount effective to inhibit the activity of TGF-β. Examples of such modulators of expression include, but are not limited to, retinoic acid, estrogen, or progesterone.

The present invention also provides a method for treating a subject having fibrosis, comprising administering to the subject an amount of ebaf or an ebaf analogue effective to treat fibrosis. The subject is preferably a mammal (e.g., humans, domestic animals, and commercial animals), and is most preferably a human. As described above, fibrosis includes, without limitation, scars, particularly scars caused by burning, radiation, chemicals, or myocardial infarct; keloid; cirrhosis; Asherman's syndrome; Meigs' syndrome; muscular dystrophies, particularly Duchenne muscular dystrophy; autoimmune disorders leading to fibrosis, including scleroderma; post-surgical fibrosis, including fibrosis induced by surgery or surgical manipulation; fibrosis induced by non-surgical manipulation; and primary pulmonary fibrosis, including Hamman Rich Syndrome and retroperitoneal fibrosis.

The ebaf or ebaf analogue of the present invention is administered to a subject in need of treatment for fibrosis in an amount which is effective to treat the fibrosis. As used herein, the phrase "effective to treat the fibrosis" means effective to ameliorate or minimize the clinical impairment or symptoms of the fibrosis. For example, where the fibrosis is Duchenne muscular dystrophy, the amount of ebaf or ebaf analogue effective to treat the fibrosis is that which can ameliorate or minimize the symptoms of Duchenne muscular dystrophy, including proximal muscle weakness and lack of co-ordination. The amount of ebaf or ebaf analogue effective to treat fibrosis in a subject in need of treatment will vary depending upon the particular factors of each case, including the type of fibrosis, the stage of fibrosis, the subject's weight, the severity of the subject's condition, and the method of administration. This amount can be readily determined by the skilled artisan.

According to the method of the present invention, ebaf or an ebaf analogue may be administered to a human or animal subject by known procedures, including, without limitation, oral administration, parenteral administration, transdermal administration, and administration through an osmotic mini-pump. Preferably, the ebaf or ebaf analogue is administered orally. The ebaf or ebaf analogue of the present invention also may be administered to a subject in accordance with any of the above-described methods for effecting in vivo contact between tissue and ebaf or an ebaf analogue.

For oral administration, the formulation of ebaf or ebaf analogue may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration, ebaf or an ebaf analogue may be combined with a sterile aqueous solution which is preferably isotonic with the blood of the patient. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be presented in unit or multi-dose containers, such as sealed ampoules or vials. The formulation may be delivered by any mode of injection, including, without limitation, epifascial, intracapsular, intracutaneous, intramuscular, intraorbital, intraperitoneal, intraspinal, intrasternal, intravascular, intravenous, parenchymatous, or subcutaneous.

For transdermal administration, ebaf or an ebaf analogue may be combined with skin penetration enhancers, such as propylene glycol, polyethylene glycol, isopropanol, ethanol, oleic acid, N-methylpyrrolidone, and the like, which increase the permeability of the skin to the ebaf or ebaf analogue, and permit the ebaf or ebaf analogue to penetrate through the skin and into the bloodstream. The ebaf/enhancer or ebaf analogue/enhance compositions also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent such as methylene chloride, evaporated to the desired viscosity, and then applied to backing material to provide a patch.

The ebaf or ebaf analogue of the present invention also may be released or delivered from an osmotic mini-pump. The release rate from an elementary osmotic mini-pump may be modulated with a microporous, fast-response gel disposed in the release orifice. An osmotic mini-pump would be useful for controlling release, or targeting delivery, of ebaf or ebaf analogue.

The present invention also provides a method for treating a defect in cell proliferation in a subject in need of treatment, comprising administering to the subject an amount of ebaf or an ebaf analogue effective to treat the defect in cell proliferation. Examples of defects in cell proliferation include, without limitation, hyperplasia and neoplasia. As used herein, "hyperplasia" refers to the abnormal multiplication or increase in the number of normal cells, in normal arrangement, in a tissue. Moreover, as used herein, "neoplasia" refers to the uncontrolled and progressive multiplication of cells under conditions that would not elicit, or would cause cessation of, multiplication of normal cells. Neoplasia results in the formation of a "neoplasm", which is defined herein to mean any new and abnormal growth, particularly a new growth of tissue, in which the growth is uncontrolled and progressive. Neoplasms include benign tumors and malignant tumors (e.g., carcinomas, lymphocytic leukemias, myeloid leukemias, lymphomas, melanomas, sarcomas, etc.). Malignant neoplasms are distinguished from benign in that the former show a greater degree of anaplasia, or loss of differentiation and orientation of cells, and have the properties of invasion and metastasis. Thus, neoplasia includes "cancer", which herein refers to a proliferation of cells having the unique trait of loss of normal controls, resulting in unregulated growth, lack of differentiation, local tissue invasion, and metastasis.

In the method of the present invention, ebaf or an ebaf analogue is administered to a subject in need of treatment for a defect in cell proliferation in an amount which is effective to treat the defect in cell proliferation. As used herein, the phrase "effective to treat the defect in cell proliferation" means effective to ameliorate or minimize the clinical impairment or symptoms of the defect in cell proliferation. For example, where the defect in cell proliferation is neoplasia, the clinical impairment or symptoms of the neoplasia may be ameliorated or minimized by diminishing any pain or discomfort suffered by the subject; by extending the survival of the subject beyond that which would otherwise be expected in the absence of such treatment; by inhibiting or preventing the development or spread of the neoplasm; or by limiting, suspending, terminating, or otherwise controlling the maturation and proliferation of cells in the neoplasm. The amount of ebaf or ebaf analogue effective to treat a defect in cell proliferation in a subject in need of treatment will vary depending on the particular factors of each case, including the type of defect in cell proliferation, the stage of the defect in cell proliferation, the subject's weight, the severity of the subject's condition, and the method of administration. This amount can be readily determined by the skilled artisan.

According to the method of the present invention, ebaf or an ebaf analogue may be administered to a human or animal subject by any known procedures, including all of those described above. Preferably, the ebaf or ebaf analogue is administered orally. The ebaf or ebaf analogue of the present invention also may be administered to a subject according to any of the above-described methods for effecting in vivo contact between tissue and ebaf or an ebaf analogue.

The present invention is described in the following Experimental Details section, which is set forth to aid in the understanding of the invention, and should not be construed to limit in any way the scope of the invention as defined in the claims which follow thereafter.

Experimental Details

1. Ebaf Inhibits TGF-β

(a) Introduction

Numerous lines of evidence support the view that the biological signaling of 25 TGF-p, and members of its superfamily, is mediated through a class of cytoplasmic proteins which are designated as Smads (for *C. elegans* sma and Drosophila "Mothers against decapentaplegic" Mad genes) (Derynck et al., 1998). TGF-β functions through binding to two receptors, and signals through the Smad family of transcription factors (FIG. 1).

Three families of Smads have been identified (Kretzschmar and Massagué, 1998). The first family is comprised of the receptor-bound Smads, or R-Smads. These proteins are directly phosphorylated by the receptor kinases. The second family includes proteins which are not direct receptor substrates, but which associate with the R-Smads; these are called Co-Smads. The third family of proteins—the Anti-Smads—inhibits the activation of the R-Smads. In vertebrates, the R-Smads include Smads 1, 2, 3, 5, and 8, the Co-Smads include Smad 4, and the Anti-Smads include Smads 6 and 7 (Kretzschmar and Massagué, 1998).

The specificity of the signaling by members of the TGF-β superfamily is mediated by the type of R-Smads which they activate. In the case of TGF-β (and activin, this includes Smads 2 and 3; for the bone morphogenic proteins (BMPs), it includes Smads 1, 5, and 8. Smad 4 acts as the common Smad that, by virtue of binding to the R-Smads, forms a heteromeric complex that is translocated to the nucleus. Within the nucleus, this complex binds a DNA-binding protein which, in the case of TGF-β and activin, is called Fast-1 (Kretzschmar and Massagué, 1998). Within this complex, Smad 4 is essential for the transcriptional activity of the promoter responsive to the ligand (e.g., PAI-1 up-regulation in response to TGF-β).

The ability of TGF-β to inhibit the activity of such kinase complexes derives in part from its regulatory effects on the cyclin-dependent kinase inhibitors, p21/WAF1/Cip1, p27Kip1, and p15. Upon treatment of cells with TGF-β, these three inhibitors bind to, and block the activities of, specific cyclin-cyclin-dependent kinase complexes, causing cell-cycle arrest. Little is known, however, of the mechanism through which TGF-β activates these cyclin-dependent kinase inhibitors. In the case of p21, TGF-β treatment leads to an increase in p21 mRNA. This increase in p21 mRNA is partly due to transcriptional activation of the p21 promoter by TGF-β. The region in the p21 promoter responsive to TGF-β signaling consists of a 10-base-pair sequence that binds transcription factors such as transcription factors Sp-1 and Sp-3; it is required for activation of the p21 promoter by TGF-β. In addition, this sequence is sufficient to drive TGF-β-mediated transcription from a previously nonresponsive promoter (Hocevar and Howe, 1998).

TGF-β also inhibits cell-cycle progression in many cell types. The TGF-β-induced cell-cycle arrest has been partially attributed to the regulatory effects of TGF-β on both the levels and the activities of the G1 cyclins and their cyclin-dependent kinase (cdk) partners. Furthermore, it has been postulated that TGF-β inhibits cell-cycle progression by blocking the late G1 activation of the cdks, thereby preventing pRb phosphorylation and S phase entry (Hocevar and Howe, 1998).

In $Rb^{+/+}$ and $Rb^{-/-}$ primary mouse embryo fibroblasts, TGF-β inhibited cdk4-associated kinase activity. However, whereas cdk2-associated kinase activity was completely inhibited by TGF-β in the wild-type cells, it was reduced only slightly in the Rb mutant cells. Moreover, at high cell density, the growth-inhibitory effects of TGF-β were no longer observed in the $Rb^{-/-}$ cells. On the contrary, TGF-β treatment promoted the growth of these mutant fibroblasts (Herrera et al., 1996; and Zhang and Jacobberger, 1996). Thus, under certain cellular-growth conditions, elimination of pRb transforms the growth-inhibitory effects of TGF-β into growth-stimulatory effects. These observations could help explain why TGF-β is often found to enhance tumorigenicity in vivo, and why inactivation of the Rb gene leads to tumorigenesis.

TGF-β was identified by its ability to cause phenotypic transformation of rat fibroblasts. Later, experiments showed that TGF-β plays an important role in the deposition of extracellular matrix and the development of fibrosis. To evaluate the role of TGF-β-1 in the pathogenesis of fibrosis, Clouthier et al. (1997) used a transgenic approach. They targeted the expression of a constitutively-active TGF-β-1 molecule to liver, kidney, and white and brown adipose tissue, using the regulatory sequences of the rat phosphoenolpyruvate carboxykinase gene. In multiple lines, targeted expression of the transgene caused severe fibrotic disease. Fibrosis of the liver occurred with varying degrees of severity, depending upon the level of expression of the TGF-β-1 gene. Overexpression of the transgene in kidney also resulted in fibrosis and glomerular disease, eventually leading to complete loss of renal function. Severe obstructive uropathy (hydronephrosis) was also observed in a number of animals. Expression in adipose tissue resulted in a dramatic reduction in total body white adipose tissue, and a marked, though less severe, reduction in brown adipose tissue, producing a lipodystrophy-like syndrome. Introduction of the transgene into the ob/ob background suppressed the obesity characteristic of this mutation; however, transgenic mutant mice developed severe hepatomegaly and splenomegaly. Clouthier et al. (1997) noted that the family of rare conditions known collectively as the lipodystrophies are accompanied in almost all forms by other abnormalities, including fatty liver and cardiomegaly. Metabolic and endocrine abnormalities include either mild or severe insulin resistance, hypertriglyceridemia, and a hypermetabolic state.

Using quantitative PCR in 15 cases of Duchenne muscular dystrophy (DMD), 13 cases of Becker muscular dystrophy, 11 spinal muscular atrophy patients, and 16 controls, Bernasconi et al. (1995) found that TGF-β-1 expression, as measured by mRNA, was greater in DMD patients than in controls. Furthermore, fibrosis was significantly more prominent in DMD than in controls. The proportion of connective tissue biopsies increased progressively with age in DMD patients, with TGF-β-1 levels peaking at 2 and 6 years of age. Bernasconi et al. (1995) concluded that expression of TGF-β-1 in the early stages of DMD may be critical in initiating muscle fibrosis, and suggested that an antifibrosis treatment might slow progression of the disease, thereby increasing the utility of gene therapy.

Choi et al. (1996) showed that, when topically applied, oligodeoxynucleotides complementary to TGF-β-1 mRNA significantly reduced scarring. Liu et al. (1995) showed that TGF-β can induce collagen formation, and mRNA expression of type I and type IV collagen, without affecting cell proliferation in cultures of human embryonic lung fibroblasts.

TGF-β also plays a role in the coagulation process. TGF-β, which is present in the blood (Grainger et al., 1995a), is released from blood clot during dissolution by plasmin (Grainger et al., 1995b). TGF-β induces the plasminogen activator (Arnoletti et al., 1995), tissue factor, and PAI-1 inhibitor, leading to the development of a hypofibrinolytic state (Dennler et al., 1998; Dong et al., 1996; and Samad et al., 1998).

(b) Methods and Results

Figure 3A:
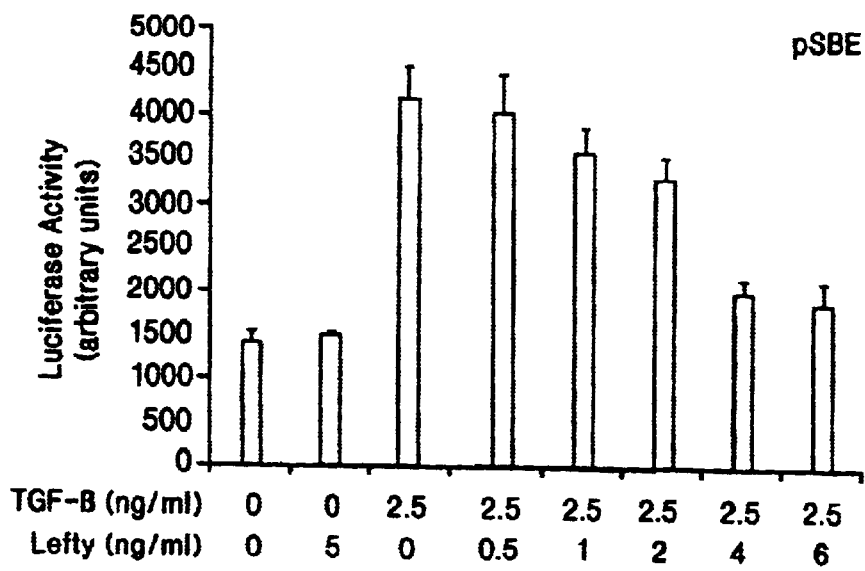
FIGS. 3A–3E demonstrate inhibition of transcriptional activity of TGF-β by ebaf. P19 cells were transfected with reporter genes (A, B: pSBE-luciferase; C: p21-luciferase; D: Cdc25-luciferase; E: CTGF-luciferase). Twenty-four hours after transfection, cells were treated with TGF-β and/or ebaf for 30 min. Cells were removed 24 h after treatment, and analyzed for luciferase activity. Values presented are the means of triplicate determinations±standard deviations.
Figure 3B:
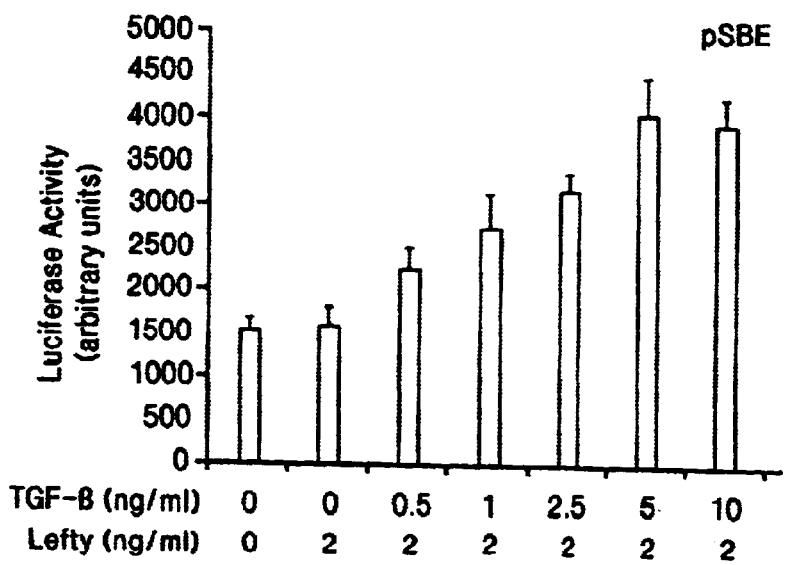

P19 totipotent embryonal carcinoma cells were transfected with the artificial construct, pSBE(Smad binding element)-Lux. In this construct, the luciferase gene is under the control of the SBE—an element in the promoter of TGF-β-responsive genes which is activated by direct binding of the TGF-β-induced transcriptional complex (Luigi et al., 1998). The luciferase activity of cells transfected with the construct was assessed in the presence of TGF-β and varying amounts of ebaf. Ebaf, in a dose-dependent fashion, inhibited the activity of the reporter (FIG. 3A). This inhibitory activity, however, could be overridden by increasing the concentration of TGF-β, thereby indicating that the extent of inhibition depends on a balanced amount of TGF-β and ebaf (FIG. 3B).

Figure 3C:
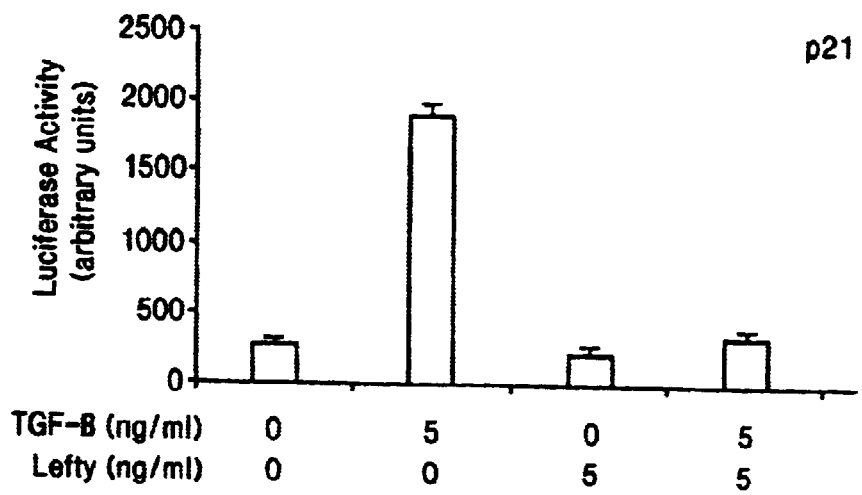
Figure 3D:
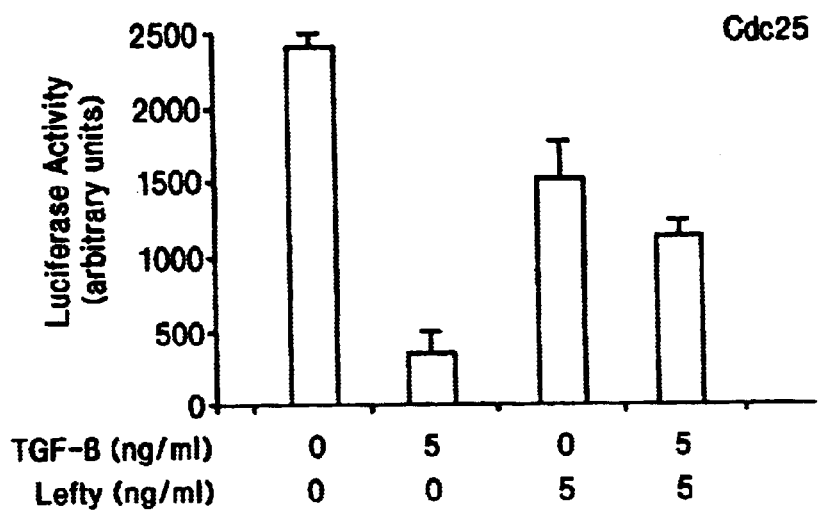

The inventors next tested the effect of ebaf on TGF-β-mediated regulation of the activity of reporters of cell cycle factors p21 and Cdc25. In untransformed epithelial cells, the G1 cell cycle events which are mediated by TGF-β include up-regulation of p21(cip1) and reduction of Cdc25 (Datto et al., 1995; Hartsough, 1997; and Iavarone and Massague, 1997). P19 cells were transfected with p21-Lux and pCdc25-Lux constructs, and the reporter activity was assessed in the presence of TGF-β and ebaf. TGF-β increased p21 reporter activity, and decreased Cdc25 reporter activity (FIGS. 3C–D). While ebaf did not have any discernible effect on its own, it significantly inhibited the reporter activity regulated by TGF-β (FIGS. 3C and 3D). Whereas Cdc25 reporter activity was reduced almost to 50%, the activity of the p21 promoter was reduced more than four-fold. These findings suggest that ebaf inhibits several well-known functions of TGF-β that control cell proliferation in epithelial cells.

Figure 3E:
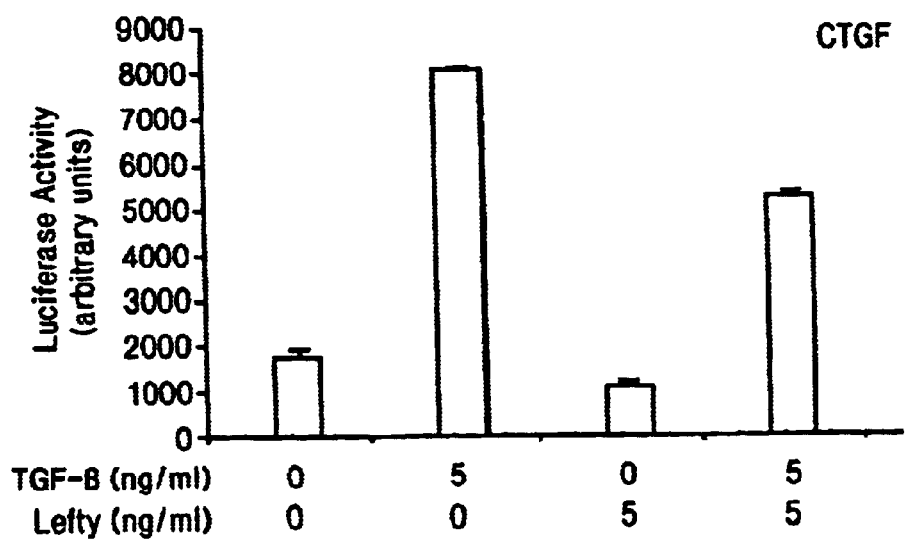

To determine whether ebaf activities are primarily confined to TGF-β-mediated control of cell cycle factors, or whether they also target other known functions of TGF-β, the inventors further tested the effect of ebaf on TGF-β-mediated connective tissue growth factor (CTGF) promoter activity. TGF-β leads to fibrogenesis by activating the transcription of CTGF, a cytokine which induces collagen synthesis by fibroblasts (Frazier et al., 1996; Grotendorst, 1997; and Duncan et al., 1999). Ebaf significantly reduced the activity of the reporter induced by 5 ng/ml of TGF-β and 15 ng/ml (not shown) of TGF-β, and brought the reporter activity to basal levels (FIG. 3E). These findings show that ebaf is a broad-range inhibitor of TGF-β activities.

Biological signaling of TGF-β involves heterodimerization of Smad2/3 with Smad4, and subsequent nuclear translocation of these proteins (Younai et al., 1994; Lin et al., 1995; Zhang et al., 1995; Choi et al., 1996; Yoshida and Hayashi, 1996; Coker et al., 1997; Heldin et al., 1997; Liu et al., 1997; Derynck et al., 1998; Howell et al., 1999; Faure et al., 2000; and Weinstein et al., 2000). Therefore, the inventors reasoned that the inhibitory effect of ebaf could be exerted on TGF-β-mediated heterodimerization of Smads, and subsequent nuclear translocation of these heteromeric complexes.

Figure 4A:
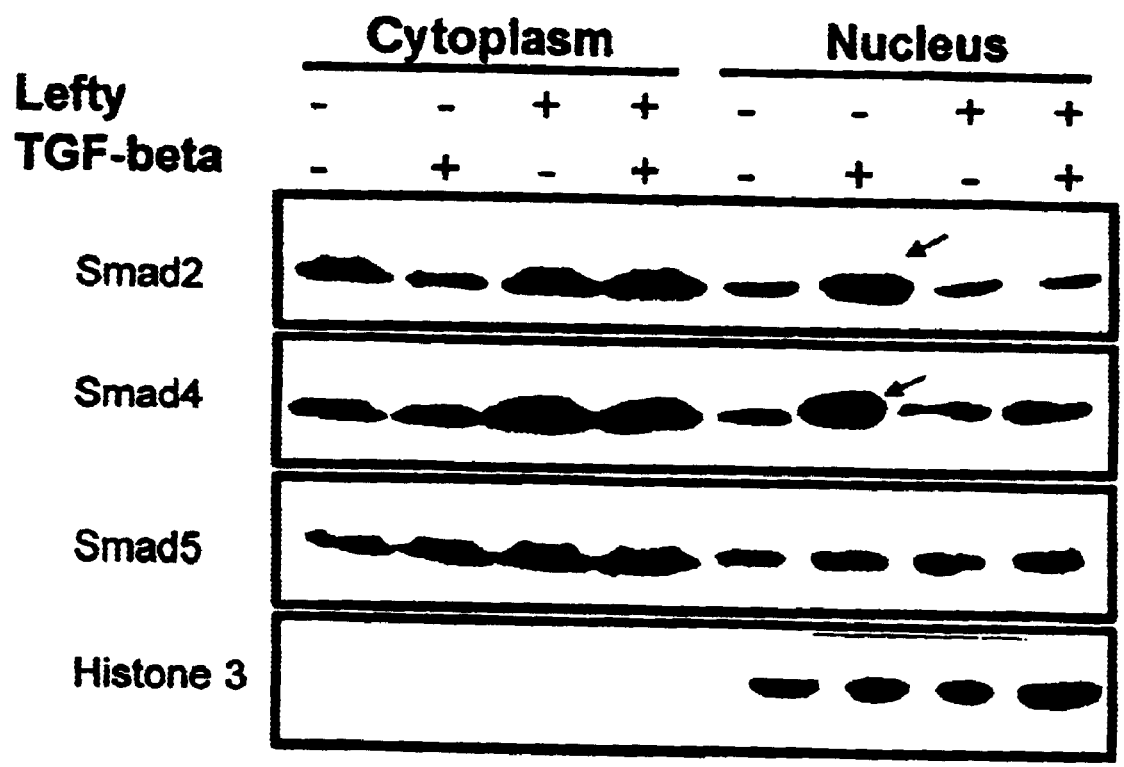
FIGS. 4A and 4B depict inhibition of TGF-β-mediated nuclear translocation of Smad2 and Smad4 by ebaf. P19 cells were treated for 30 min, with medium alone (control), TGF-[ (]5 ng/ml), recombinant ebaf (5 ng/ml), or TGF-β (5 ng/ml) plus ebaf (5 ng/ml). A: The cytosolic and nuclear fractions were prepared from the treated cells, and equal amounts of protein (10 g/lane) were subjected to Western blot analysis for Smad2, Smad4, Smad5, and Histone 3. The localization of Histone 3 in the nuclear fraction, and the absence of Histone 3 from the cytosolic preparation, show that these preparations were not cross-contaminated. Arrows point to the accumulated Smad2 and Smad4 in the nuclear lysates. B: Smad4 was localized by immunoperoxidase staining in the treated cells. Arrows point to nuclear Smad4. panel a: control cells treated with medium alone; panel b: cells treated with TGF-β; panel c: cells treated with ebaf; panel d: cells treated with TGF-β and ebaf; percentage of cells showing nuclear staining: control: 2%; TGF-β: 25%; ebaf: 3%; and TGF-β +ebaf: 1%
Figure 4B:
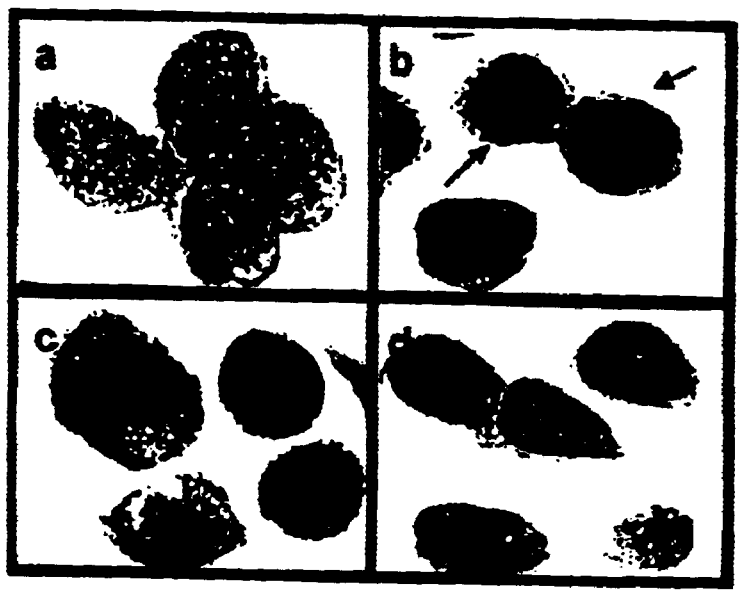

As a first step towards elucidation of such a role, P19 cells were treated with TGF-β, in the presence and absence of ebaf. After 1 h of treatment, the cytosol and nuclear lysates of these cells were subjected to Western blotting for Smad2, Smad4, and Smad 5. In comparison with the control cells, TGF-β led to the accumulation of Smad2 and Smad4 in the nuclei of treated cells (FIG. 4A; arrows). TGF-β did not have any effect on nuclear translocation of Smad5, which is an intracellular mediator of the BMP signaling pathway (Kawabata et al., 1998). While ebaf did not change the amount of Smads in the cytosol or the nuclei of the treated cells, it did inhibit the TGF-β-induced nuclear translocation of both Smad2 and Smad4 (FIG. 4A). Immunolocalization of Smad4 in P19 cells treated with TGF-β or ebaf showed nuclear accumulation of Smad4 by TGF-β treatment. In contrast, ebaf did not increase the amount of nuclear Smad4 on its own; rather, it inhibited the TGF-β-induced Smad4 nuclear accumulation (FIG. 4B). These findings show that ebaf prevents the TGF-β-mediated nuclear accumulation of the Smad2/4 complex required for gene transcriptional activity.

Figure 5:
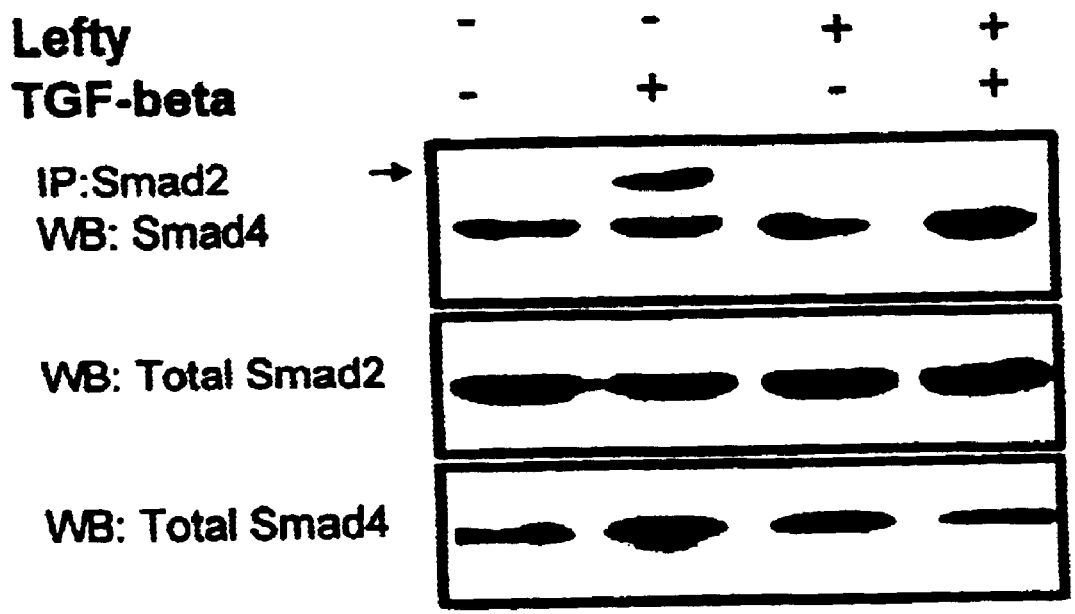
FIG. 5 depicts inhibition of TGF-β-mediated heterodimerization of Smad2 and Smad4 by ebaf. P19 cells were treated for 30 min with medium alone (control), TGF-β (5 ng/ml), ebaf (5 ng/ml), or TGF-β (5 ng/ml) plus ebaf (5 ng/ml). The proteins in the nuclear preparations were immunoprecipitated with an antibody to Smad2, and the immunoprecipitates were subjected to Western blot analysis for Smad4 (upper panel). The cell lysates were analyzed for Smad2 and Smad4 by Western blotting, in order to assess the overall amount of each protein (two lower panes). IP: immunoprecipitation; WB: Western blotting

In light of these findings, the inventors assessed the extent to which ebaf can inhibit the TGF-β-mediated heterodimerization of Smad2 with Smad4. Smad2 was immunoprecipitated from the nuclear fraction of P19 cells which had been treated with TGF-β and/or ebaf. The immunoprecipitates were subjected to Western blotting for Smad4 (FIG. 5). As expected, in the TGF-β-treated cells, Smad4 was present in the Smad2 immunoprecipitate, showing that it had heterodimerized with Smad2 (FIG. 5). Ebaf had no effect on this event, but did prevent the TGF-β heterodimerization of Smad4 with Smad2 (FIG. 5). Treatment of cells with TGF-β or ebaf did not lead to any detectable changes in the total amount of Smad2 or Smad4 (FIG. 5).

Figure 6:
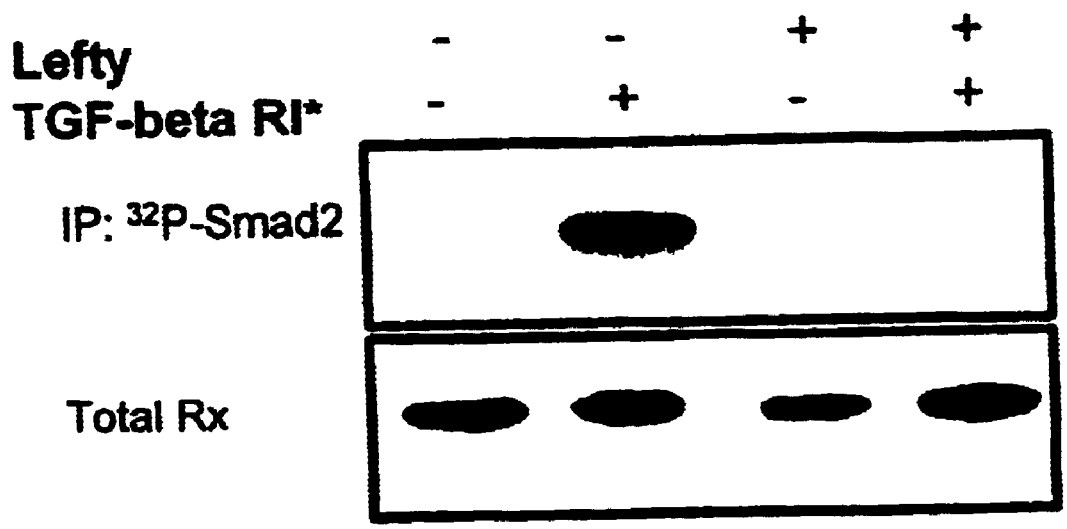
FIG. 6 illustrates inhibition of TGF-β-mediated phosphorylation of Smad2 by ebaf. P19 cells were treated for 30 min in culture medium alone (control), or in culture medium supplemented with TGF-β (5 ng/ml), recombinant ebaf (5 ng/ml), or TGF-β (5 ng/ml) plus ebaf (5 ng/ml), in the presence of 0.15 μCi [$^{32}$P]-orthophosphate per ml. Smad2 was immunoprecipitated with Smad2 antibody, and the immunoprecipitate was subjected to SDS-PAGE followed by autoradiography (upper panel). The overall amount of Smad2 was assessed by Western blotting of cell lysates (lower panel). RI: TGF-β receptor type I; WB: Western blotting; $^{32}$P: [$^{32}$P]-orthophosphate; Rx: radioactivity FIGS. 7A and 7B demonstrate inhibition by ebaf of transcriptional activity of constitutively-active TGF-β receptor type I. A: P19 cells were transfected with pSBE-Lux reporter construct. Twenty-four hours after transfection, cells were treated for 30 min with cell culture medium alone (control), or medium supplemented with TGF-β (5 ng/ml), recombinant ebaf (5 ng/ml), or TGF-β (5 ng/ml) plus ebaf (5 ng/ml). Cells were removed 24 h after treatment, then analyzed for luciferase activity. Values presented are the means of triplicate determinations±standard deviations. B: P19 cells were transfected with the constitutively-active TGF-β receptor type I. Transfected cells then were treated for 30 min, in the presence of 0.15 μCi [$^{32}$P]-orthophosphate (10 μCi/ml), with cell culture medium alone (control), or medium supplemented with TGF-β (5 ng/ml), ebaf (5 ng/ml), or TGF-β (5 ng/ml) plus ebaf (5 ng/ml). Smad2 was immunoprecipitated, and the immunoprecipitates were subjected to SDS-PAGE followed by Western blotting and autoradiography (upper panel). The overall amounts of TGF-β receptor type I and Smad2 were assessed by Western blotting (two lower panels). RI: TGF-β receptor type I; WB: Western blotting; $^{32}$P: [$^{32}$P]-orthophosphate; IP: immunoprecipitation FIGS. 8A and 8B demonstrate competition between ebaf and TGF-β for binding to TGF-β receptor type I. P19 cells were incubated with radioiodinated TGF-β (10 μCi/ml) in the presence of varying concentrations of ebaf. The receptor-bound TGF-β then was cross-linked to the receptor in the presence of DSS. A: The cell lysates were subjected to immunoprecipitation, using an antibody to TGF-β receptor type I, and then SDS-PAGE, followed by Western blotting and autoradiography (upper panel). The overall amount of cell radioactivity was assessed by subjecting a total amount of 1 μCi/lane from the cell lysate to SDS-PAGE and autoradiography (middle panel). The overall amount of TGF-β receptor was analyzed by Western blotting (lower panel). B: The Smad2 proteins in the cell lysates were immunoprecipitated, and the immunoprecipitates were subjected to SDS-PAGE and autoradiography (upper panel). The overall amount of radioactivity was assessed by subjecting the cell lysate (1 μCi/lane) to gel electrophoresis and autoradiography (second panel from top). The total amounts of TGF-β receptor type I and Smad2 were analyzed by Western blotting (two lower panels). RI: TGF-β receptor type I; WB: Western blotting; $^{32}$P: [32P]-orthophosphate; IP: immunoprecipitation; Rx: radioactivity

Formation of the Smad heteromeric complexes requires phosphorylation of the Smad2/3 proteins by the serine kinase activity of TGF-β receptor type I, after binding of TGF-β to its receptors (Younai et al., 1994; Lin et al., 1995; Zhang et al., 1995 Choi et al., 1996; Yoshida and Hayashi, 1996; Coker et al., 1997; Heldin et al., 1997; Liu et al., 1997; Derynck et al., 1998; Howell et al., 1999; Faure et al., 2000; and Weinstein et al., 2000). To determine whether ebaf exerts its function by interfering with this essential step, the inventors next examined the effect of ebaf on TGF-β-mediated Smad2 phosphorylation (FIG. 6). P19 cells were treated with TGF-β, ebaf, or both, in the presence of [$^{32}$P]-orthophosphate, in order to label phosphorylated proteins. Smad2 proteins in the lysates were immunoprecipitated. Immunoprecipitates were subjected to SDS-gel electrophoresis and Western blotting, followed by autoradiography. As expected, TGF-β led to the phosphorylation of Smad2. Although, ebaf did not alter the phosphorylation of Smad2, it reduced the TGF-β-mediated Smad2 phosphorylation by 60% (FIG. 6).

Figure 7A:
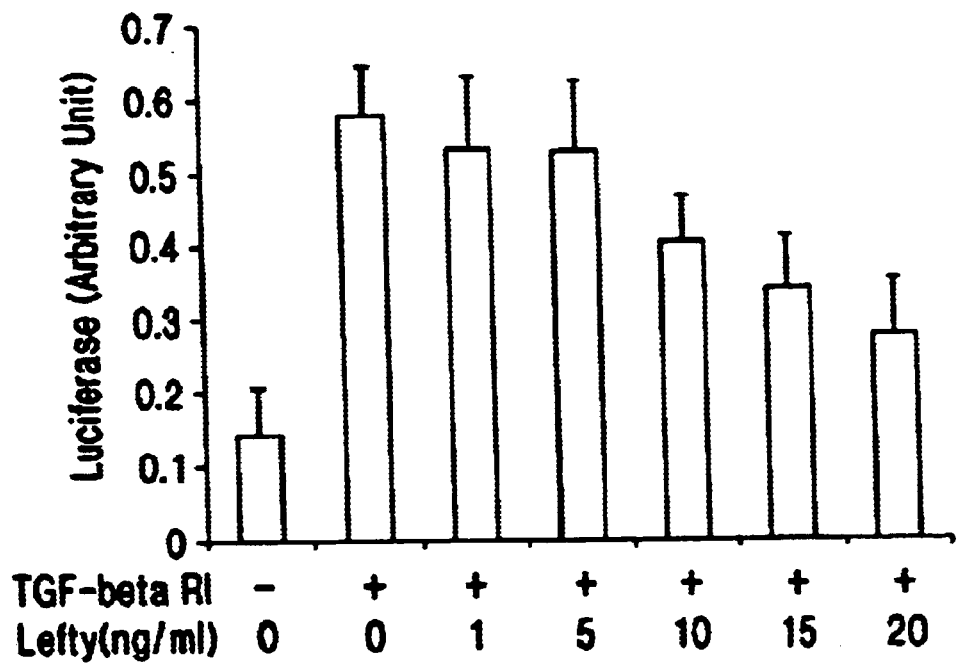
Figure 7B:
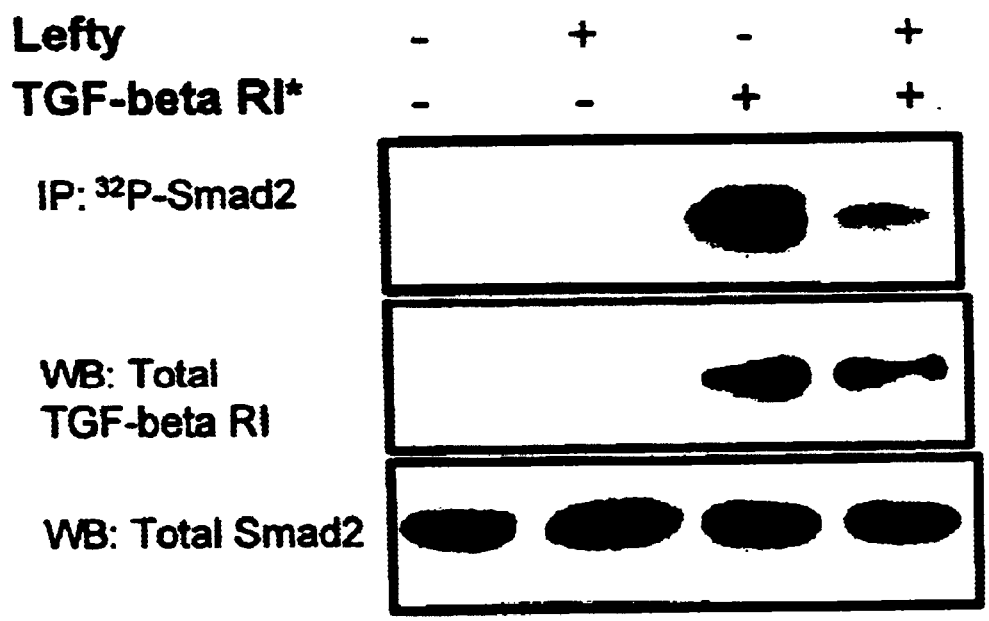

To exert its function, TGF-β oligomerizes type I and type II receptors on the cell surface (Wrana et al., 1992; and Bassing et al., 1994). In the complexes which are formed, type I receptors get phosphorylated by the constitutively-active type II receptors (Wrana et al., 1994). To ascertain whether ebaf has inhibitory activity because it interferes with the binding of TGF-β to its receptors and/or the oligomerization of the receptors, or whether ebaf's inhibitory activity is independent of these events, the inventors first analyzed the effect of ebaf on gene transcription driven by a constitutively-active form of TGF-β receptor type I. The receptor was transfected along with pSBE-Lux construct into P19 cells, and ebaf s effect on reporter activity was assessed. Ebaf, in a dose-dependent fashion, inhibited the activity of the reporter induced by the receptor (FIG. 7A). Moreover, ebaf inhibited by 80% the phosphorylation of Smad2 by the receptor (FIG. 7B).

Figure 8A:
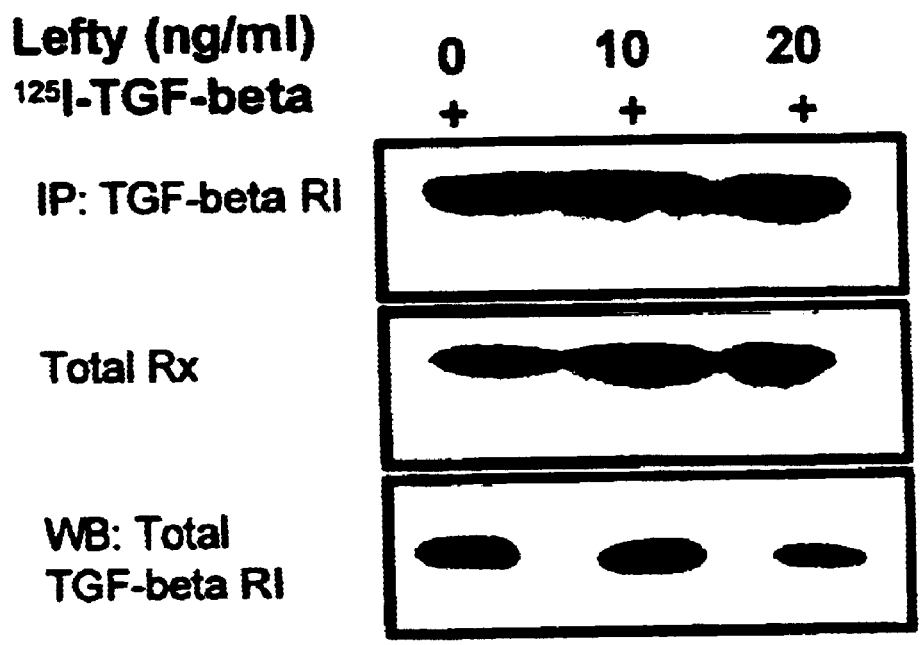
Figure 8B:
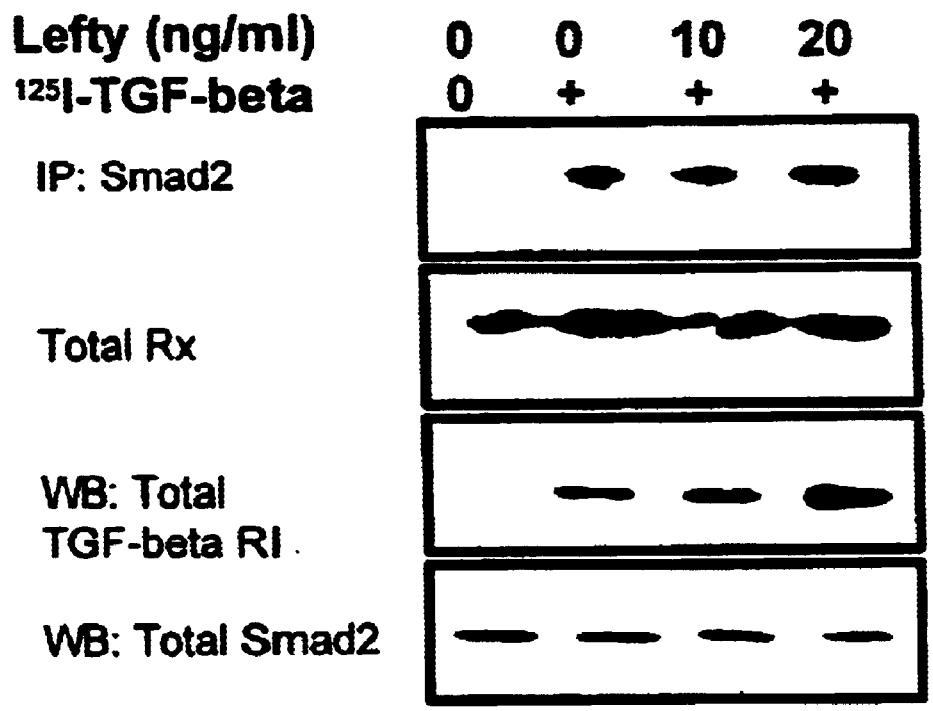

The inventors further analyzed the interaction of ebaf with the TGF-β receptor as a possible mechanism for the inhibitory activity of ebaf. Radioiodinated TGF-β was cross-linked to the TGF-β receptors in the presence of varying amounts of ebaf. The receptor cross-linked to TGF-β was immunoprecipitated by an antibody to TGF-β receptor type I. The immunoprecipitates then were subjected to gel electrophoresis, followed by autoradiographic assessment of the amount of radioactivity. Ebaf, at its biologically-effective doses, failed to inhibit the binding of TGF-β to receptor type I (FIG. 8A); it also failed to inhibit the amount of Smad2 bound to the receptor immunoprecipitated by an antibody to Smad2 (FIG. 8B). These findings show that inhibition by ebaf of TGF-β signaling does not involve competition between TGF-β and ebaf for binding to the type I receptor.

One possibility for ebaf's inhibition of TGF-β-mediated activities is induction of expression of inhibitory Smad proteins (anti-Smads). Two Smad proteins, Smad6 and Smad7, inhibit the actions of TGF-β intracellularly. Smad7 interferes with TGF-β signaling by interaction with, and inhibition of phosphorylation of, receptor-bound Smads (Hayashi et al., 1997; and Nakao et al., 1997). Overexpression of Smad7 has been shown to be responsible for the antagonistic effect of IFN-γ on TGF-β-mediated cellular functions (Ulloa et al., 1999). Smad6 forms stable associations with type I receptors, and interferes with the phosphorylation of Smad2 and its heterodimerization with Smad4; however, Smad6 does not inhibit the phosphorylation of Smad3 (Imamura et al., 1997; Nakayama et al., 1998; and Hata et al., 1998).

Figure 9A:
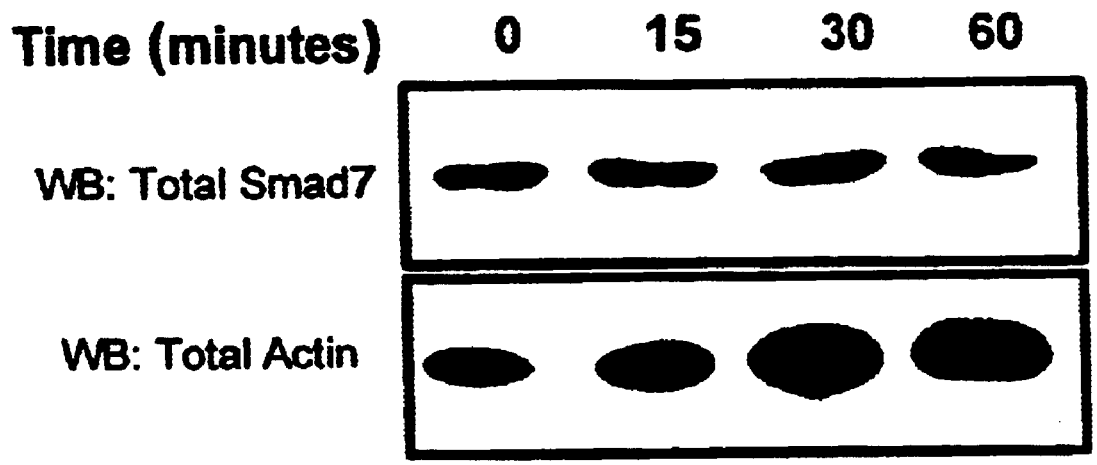
FIGS. 9A and 9B illustrate the effect of ebaf on Smad7 and total protein synthesis. A: P19 cells were treated for 30 min with cell culture medium supplemented with varying concentrations of ebaf, as shown. The proteins in the cell lysates were subjected to Western blot analysis for Smad7. Equal loading was assessed by Western blotting the cell lysates for actin. B: P19 cells were transfected with a constitutively-active form of TGF-β receptor type I. Twenty-four hours after transfection, cells were treated with cyclohexamide (20 g/ml) for 1 h. Cells then were treated for 30 min with culture medium alone (control), or medium supplemented with TGF-β (5 ng/ml), ebaf (5 ng/ml), or TGF-β (5 ng/ml) plus ebaf (5 ng/ml). Smad2 was immunoprecipitated from the cell lysates, and the immunoprecipitates were subjected to SDS-PAGE and autoradiography (upper panel). The overall amount of radioactivity was assessed by gel electrophoresis and autoradiography of the cell lysates (1 μCi/lane) (lower panel). WB: Western blotting; $^{32}$P: [$^{32}$P]-orthophosphate; IP: immunoprecipitation
Figure 9B:
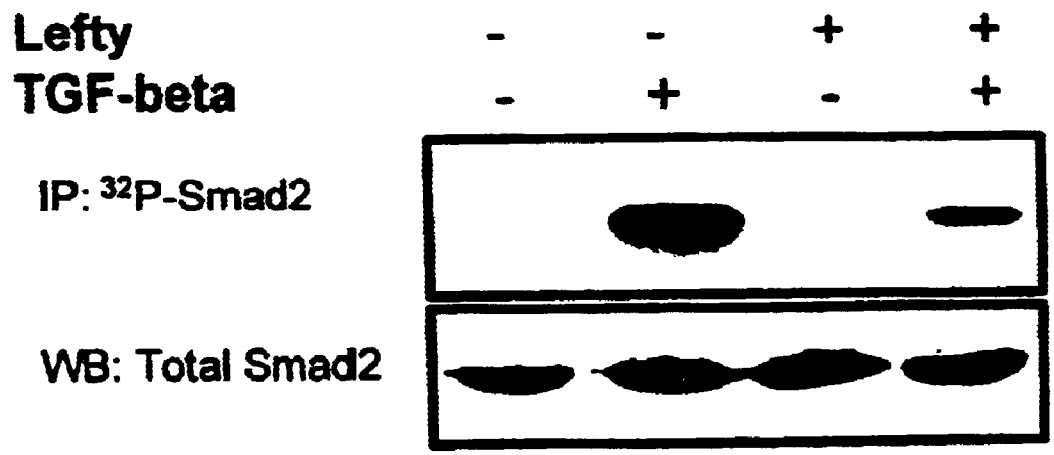

To determine whether the inhibitory activity exhibited by ebaf involves synthesis of Smad7, P19 cells were treated with ebaf for various periods of time. The cell lysates then were subjected to Western blot analysis for Smad7 (FIG. 9A). Ebaf did not induce any change in the total amount of Smad7. Similarly, treatment of cells with ebaf failed to induce any change in the amount of Smad6 (data not shown). To determine whether the inhibitory activity of ebaf requires synthesis of any other protein, the phosphorylation of Smad2 was analyzed, in the presence and absence of ebaf, in P19 cells that had been treated with cyclohexamide and transfected with constitutively-active TGF-β receptor type I. In the presence of cyclohexamide, ebaf inhibited Smad2 phosphorylation by the active TGF-β receptor type I (FIG. 9B). Taken together, these findings show that inhibition of the activity of TGFβ by ebaf does not require synthesis of Smad6, Smad7, or any other protein.

Accumulation of Smads is induced by receptor-mediated phosphorylation at their carboxy termini, and can be inhibited by MAP kinase-mediated phosphorylation at their central regions. For this reason, the effect of ebaf on MAP kinase was assessed for the potential to restrict Smad activation. A conditioned medium of cells transfected with lefty-A (ebaf) and lefty-B was able to activate the MAPK pathway. A conditioned medium of cells transfected with the GGKG lefty-A (ebaf) mutant cDNA, which led to loss of the 34-kD form of the lefty-A (ebaf) protein into the culture medium, also exhibited this activity (FIG. 10, upper panel). However, a conditioned medium of cells transfected with the GHGR lefty-A (ebaf) mutant, which led to loss of the 28-kD protein, did not show this activity.

Figure 11:
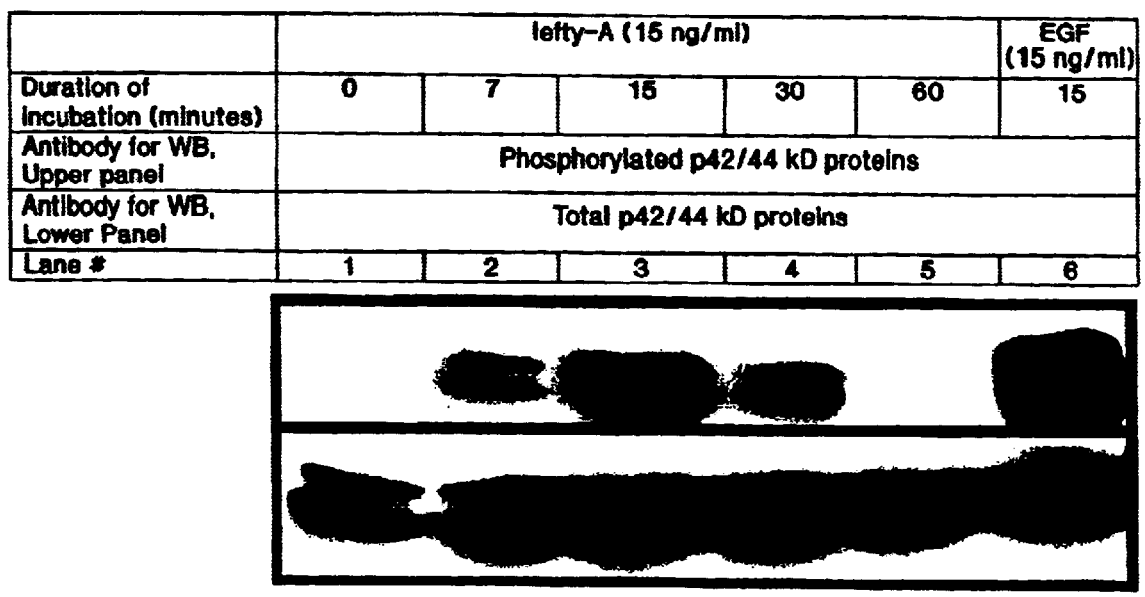
FIG. 11 demonstrates activation of the MAPK pathway by recombinant ebaf. P19 cells were incubated with 15 ng/ml of the recombinant ebaf for the indicated durations. As a positive control, cells were treated with 15 ng/ml of epidermal growth factor (EGF) for 15 min. After cytokine treatment, activated phosphorylated (upper panel) and total (lower panel) forms of p42/p44-kD MAPK were visualized by Western blotting, as indicated below.

To demonstrate that this activity was due to ebaf protein in the culture medium, the effect of the medium was examined in the presence of varying amounts of affinity-purified rabbit polyclonal antibody specific to ebaf (FIG. 10, middle panel). The activity of the conditioned medium was inhibited, in a dose-dependent fashion, in the presence of the antibody. To directly show that this activity was mediated by the 28-kD form of the ebaf protein, the activity of the 26-kD recombinant E. coli ebaf protein, which corresponded to the non-glycosylated 28-kD ebaf, was tested (FIG. 10, lower panel). The 26-kD recombinant protein induced MAPK activation in a dose-dependent fashion. Activation of MAPK by ebaf was validated by Western blot analysis (FIG. 11). Recombinant E. coli ebaf induced the phosphorylation of the p42/44-kD proteins in 7 min; this phosphorylation reached a maximum within 15 min of incubation with ebaf.

The inventors also tested the effect on the c-Jun N-terminal kinase (JNK) pathway of culture media containing cells transfected with lefty-A (ebaf), lefty-B, and the 26-kD recombinant E. coli-produced ebaf protein. However, no effect on the JNK pathway was observed.

2. Ebaf Leads to Fibroblast Death (a) Introduction

Transforming growth factor beta (TGF-β) protects fibroblasts from apoptosis-inducing signals and promotes fibroblast proliferation (Tredget et al., 2000; and Fine and Goldstein, 1987). TGF-β inhibits apoptosis by causing cellular production of a distinct set of proteins. Specifically, the treatment of NRK 536 fibroblasts with TGF-β caused a reversible transformed phenotype (Vossbeck et al., 1995). A 15-kD membrane adhesion protein, called TGF-β induced factor 2 (TIF2), has been identified as one of the proteins induced by TGF-β which mediates this transforming ability. This factor is able to provide resistance to TGF-β induced apoptosis (Carey and Chang, 1998). Fibrosis is a process that involves undesirable proliferation of fibroblasts. TGF-β in such lesions promotes fibrosis by promoting proliferation and inhibiting fibroblast apoptosis. Identification of a factor that counteracts this action of TGF-β could be useful therapeutically. The inventors have found that ebaf leads to fibroblast death. This specificity renders ebaf particularly useful in the treatment of fibrotic disorders.

(b) Materials and Methods

Retroviral Vector Expression Plasmid Construction: LX-Ebaf-IRES-eGFP (LEIG): Plasmid LX-ebaf was double digested with Sph I and Xho I to generate a 6155-bp fragment. Oligonucleotide primers NS204 (5'aaagatatcgcatgccctctccctccccccccctaacg3') (SEQ ID NO:3) and NS205 (5'ttgatatcctcgagttacttgtacagctcgtccatgcc3') (SEQ ID NO:4) were used as PCR primers with plasmid pIRES-eGFP (Clontech) to generate a 1338 bp Sph I/Xho I IRES-eGFP fragment which was cloned into the 6155-bp LX-ebaf fragment to generate plasmid LEIG. This retroviral vector plasmid can be used to generate retroviral vector particles for transduction of various cells and cell lines when transfected into retroviral packaging cell lines such as PA317 and GP+E86.

Mammalian Expression Plasmid Construction: The sense and anti-sense orientations of the ebaf cDNA were constructed using plasmid pAdCMV5 (Quantum Biotechnologies Inc., Montreal, Canada) in which ebaf gene expression is regulated by the cytomegalovirus immediate early promoter. A 1.2-kb BamHI/AflIII ebaf cDNA fragment containing minimal 5' and 3' untranslated regions was isolated from plasmid pBluescript2SK-ebaf, filled with T4 DNA polymerase, and cloned into Pmel-digested pAdCMV5. Restriction mapping and flanking DNA sequencing confirmed the orientation of the resulting ebaf expression plasmids.

MTT assay: The MTT assay was performed as per manufacturer's instructions (SIGMA BioSciences):

1. CCD19Lu cells that were treated in duplicate wells of 6-well dishes were washed twice with PBS.
2. 450 μl of DMEM supplemented with 10% heat-inactivated FBS was added to each well and to two blank wells that served as medium-only controls.
3. 50 μl of MTT Solution (SIGMA BioSciences, cat. #M0283) was added to each well, and cells were incubated for 4 h at 37° C. in 5% $CO_2$.
4. 500 μl of MTT Solvent (SIGMA BioSciences, cat. #M0408) was added to the wells and repeatedly triturated with the cells using a pipette to lyse the cells and dissolve the formazan crystals.
5. Aliquots of the cell lysates were transferred in triplicate to a 96-well microtiter plate.
6. An ELISA plate reader was used to measure the amount of formazan crystals generated from living cells. The test wavelength was 540 nm, and the reference wavelength was 690 nm.

(c) Results

The inventors used a mammalian expression plasmid to stably express ebaf in both an epithelial (293) and a fibroblastic cell line (NIH3T3). Both cell lines produced ebaf. However, the NIH3T3 cell line lost its ability to synthesize ebaf within weeks after transfection, whereas the 293 cells were capable of producing ebaf for a year and a half post-transfection while maintained under G418 selective pressure for plasmid maintenance. These findings suggest that the expression of ebaf is detrimental to NIH3T3 cells, and that the ebaf-positive cells are lost.

The inventors also transfected 293 cells and a fibroblastic cell line, PA137, with a retroviral vector expression plasmid (LEIG) capable of expressing both ebaf and a green fluorescent protein (GFP). Another retroviral vector expression plasmid, expressing only GFP (LG), was used as a control. The 293 cells expressed both ebaf and GFP upon transfection with LEIG, and expressed only GFP upon transfection with LG. The PA137 cells that were transfected with LG expressed GFP. Interestingly, the PA137 cells that were transfected with LEIG resulted in large amounts of cell death, with little or no GFP expression, suggesting toxicity of ebaf overexpression in these cells.

The inventors then proceeded to treat the human fibroblastic cell line, CCD19Lu, with 24-hour-conditioned medium collected from both 293 cells and 293 cells that were stably transfected with LEIG and known to express both ebaf and GFP. The conditioned medium was replaced approximately every two days with fresh conditioned medium on the CCD19Lu cells. The CCD19Lu cells treated with 293 conditioned medium (without ebaf and GFP) continued to grow and proliferate normally. In contrast, the CCD19Lu cells treated with conditioned medium from the 293 cells expressing both ebaf and GFP resulted in a large amount of cell death starting on the second day of treatment.

Figure 12:
FIG. 12 depicts the appearance of CCD19Lu cells treated with the medium from wild-type 293 cells (−), and those treated with the medium of 293 cells producing ebaf (+). The CCD19Lu cells had a normal appearance, and exhibited a spindle cell morphology. In contrast, most CCD19Lu cells treated with the culture medium were lost. Few cells that remained attached to the dish had abnormal morphology. Some cells were round, and had detached from the dish (arrows).
Figure 13:
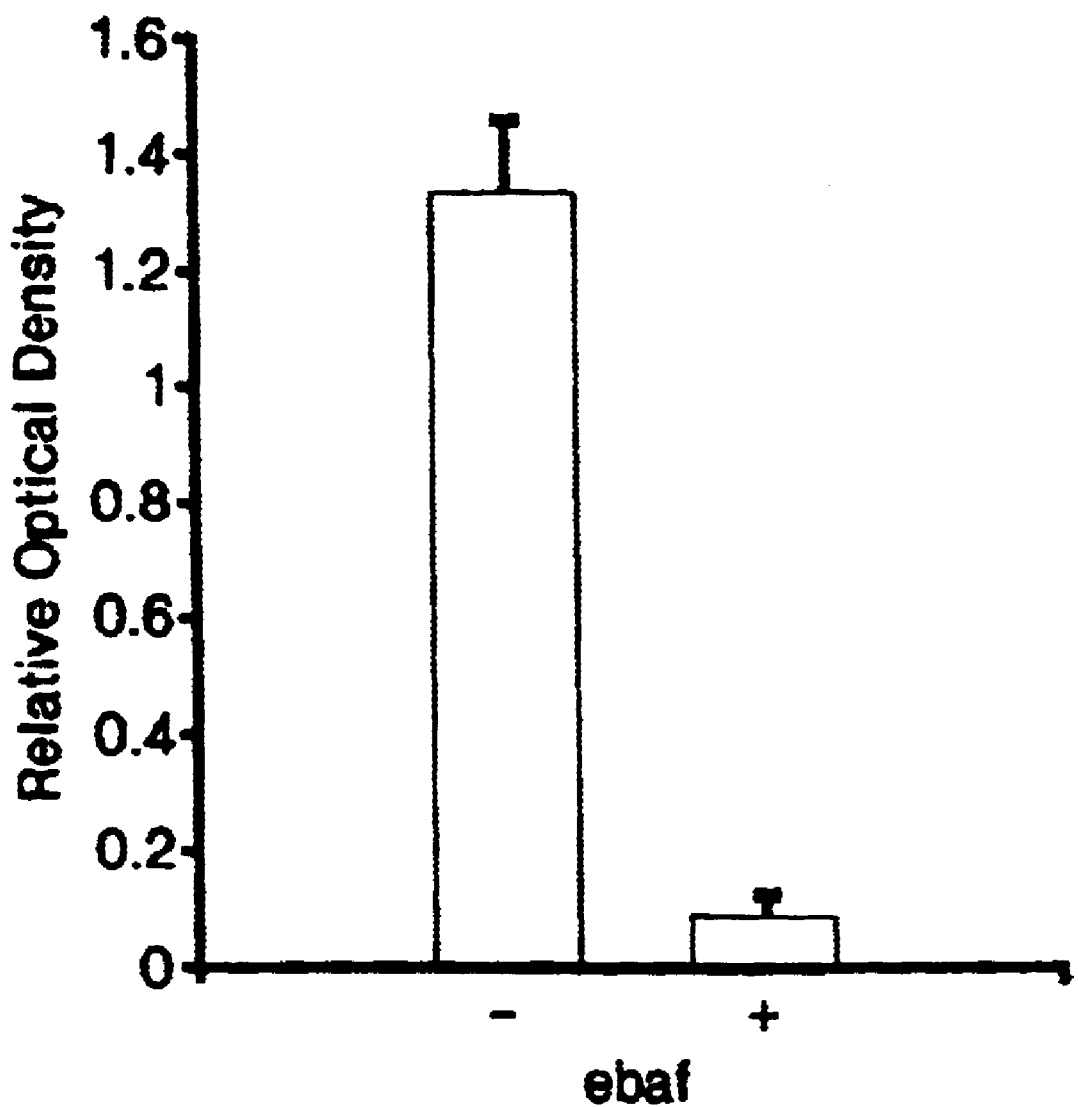
FIG. 13 depicts the results of the MTT assay of CCD19Lu cells treated with 293 conditioned medium (−ebaf) or 293 ebaf-containing medium (+ebaf) 9 days after initial treatment. The MTT assay was performed as described in the text, and results are expressed as relative optical densities.

Initially, the CCD19Lu cells developed an abnormal morphology, including loss of cytoplasm and development of a spindly appearance, followed by rounding and detachment from the dish (FIG. 12). An MTT assay (a measure of live cells) was performed on the treated CCD19Lu cells at day 9 following initial treatment (FIG. 13). At this time, microscopic examination of the CCD19Lu cells indicated that the cells treated with 293 conditioned medium were healthy, confluent; cultures of cells. Conversely, the CCD19Lu cells treated with the 293 medium containing ebaf were either dead or appeared to be undergoing cell death. Results of the MTT assay indicate that there is at least a 15-fold decrease in the number of live cells in the ebaf containing medium compared to the control containing only 293 conditioned medium.

3. Ebaf Leads to Regression of Tumors

The inventors tested the effect of ebaf on growth of fibroblastic cells by injecting into nu/nu mice GP+E86 cells transduced with a retroviral vector expressing green fluorescent protein (LG) or green fluorescent protein (GFP) and ebaf (LEIG). Cells were injected both subcutaneously and intraperitoneally. As shown in FIG. 14, after 3 wk, the size and volume of the subcutaneous and peritoneal tumors were significantly smaller in the LEIG-injected mice, as compared with the animals injected with LG cells.

List of Cited Publications

1. Arnoletti et al., *Cancer*, 76(6):998–1005, September 1995.
2. Bassing et al., *J. Biol. Chem.*, 269(21):14861–64, 1994.
3. Bernasconi et al., *J. Clin. Invest.*, 96:1137–44, 1995.
4. Berndt et al., *Histochem. J.*, 27(12):1014–20, December 1995.
5. Bettinger et al., *Plast. Reconstr. Surg.*, 98(5):827–33, October 1996.
6. Bottinger et al., *EMBO J.*, 16:2621–33, 1997.
7. Carey and Chang, *Biochem. Biophys. Res. Commun.*, 249(1):283–6, 1998.
8. Choi et al., *Immunol. Cell. Biol.*, 74(2):144–50, April 1996.
9. Clark et al., *J. Cell Physiol.*, 170(1):69–80, January 1997.
10. Clouthier et al., *J. Clin. Invest.*, 100:2697–713, 1997.
11. Coker et al., *Am. J. Pathol.*, 150(3):981–91, March 1997.
12. Datto et al., *Proc. Natl Acad. Sci. USA*, 92(12):5545–49, 1995.
13. Dennler et al., *EMBO J.*, 17(11):3091–100, June 1998.
14. Dong et al., *J. Biol. Chem.*, 271(47):29, 969–77, November 1996.
15. Derynck et al., *Cell*, 95(6):737–40, December 1998.
16. Duncan et al., *FASEB J.*, 13(13):1774–86, 1999.
17. El-Gamel et al., *Eur. J. Cardiothorac. Surg.*, 13(4):424–30, April 1998.
18. Faure et al., *Development*, 127(13):2917–31, 2000.
19. Fine and Goldstein, *J. Biol. Chem.*, 262(8):3897–902, March 1987.
20. Franzen and Dahlquist, *In Vitro Cell Dev. Biol. Anim.*, 30A(7):460–63, 1994.
21. Frazier et al., *J. Invest. Dermatol.*, 107(3):404–11, 1996.
22. Grainger et al., *Clin. Chim. Acta*, 235(1):11–31, February 1995a.
23. Grainger et al., *Nat. Med.*, 1(9):932–37, September 1995b.
24. Grotendorst, G. R., *Cytokine Growth Factor Rev.*, 8(3):171–79, 1997.
25. Hall et al., *Anticancer Res.*, 16(4A):1755–58, July-August 1996.
26. Han, D. C., *J. Am. Soc. Nephrol.*, 10(9):1891–99, September 1999.
27. Hao et al., *J. Mol. Cell. Cardiol.*, 31(3):667–78, March 1999.
28. Hartsough and Mulder, *Pharmacol. Ther.*, 75(1):21–41, 1997.
29. Hata et al., *Genes Dev.*, 12(2):186–97, 1998.
30. Hayashi et al., *Cell*, 89(7):1165–73, 1997.
31. Heldin et al., *Nature*, 390:465–71, 1997.
32. Herrera et al., *Mol. Biol. Cell.*, 7(9):1335–42, September 1996.
33. Hocevar and Howe, *Miner. Electrolyte Metab.*, 24(2–3):131–35, 1998.
34. Howell et al., *Dev. Biol.*, 214(2):354–69, 1999.
35. Imamura et al., *Nature*, 389:622–26, 1997.
36. Iavarone and Massagué, *Nature*, 387:417–22, 1997.
37. Kawabata et al., *Cytokine Growth Factor Rev.*, 9(1):49–61, 1998.
38. Khalil et al., *Am. J. Respir. Cell. Mol. Biol.*, 14(2):131–38, February 1996.
39. Kornmann, M., *Int. J. Cancer*, 83(2):247–54, October 1999.
40. Kosaki et al., *Am. J. Hum. Genet*, 64(3):712–21, March 1999.
41. Kothapalli et al., *J. Clin. Invest.*, 99(10):2342–50, 1997.
42. Kretzschmar and Massagué, *Curr. Opin. Genet. Dev.*, 8(1):103–11, February 1998.
43. Lee, T. Y., *Ann. Plast. Surg.*, 43(2):179–84, August 1999.
44. Lin et al., *Ann. Surg.*, 222(2):146–54, August 1995.
45. Liu et al., *Chung Hua Chieh Ho Ho Hu Hsi Tsa Chih*, 18(5):287–89, 317–18, October 1995.

46. Liu et al., *Proc. Natl Acad. Sci. USA*, 94:10669–74, 1997.
47. Luigi et al., *J. Biol. Chem.*, 273:21145–52, 1998.
48. Martinet et al., *Arch. Toxicol. Suppl.*, 18:127–39, 1996.
49. Meno et al., *Nature*, 381:151–55, 1996.
50. Messadi, D. V., *Front. Biosci.*, 3: A16–A22, February 1998.
51. Morton and Barrack, *Cancer Res.*, 55(12):2596–602, June 1995.
52. Mur et al., *Cell Biol. Int.*, 22(9–10):679–84, 1998.
53. Nakao et al., *Nature*, 389(6651):631–35, 1997.
54. Nakayama et al., *Genes Cells*, 3(6):387–94, 1998.
55. O'Kane and Ferguson, *Int. J. Biochem. Cell. Biol.*, 29(1):63–78, January 1997.
56. Oulad-Abdelghani et al., *Int. J. Dev. Biol.*, 42(1):23–32, 1998.
57. Padgett et al., *Bioessays*, 20(5):382–90, 1998.
58. Polo et al., *J. Burn Care Rehabil.*, 18(6):477–82, November-December 1997.
59. Querfeld et al., *J. Dermatol. Sci.*, 21(1):13–22, September 1999.
60. Randall and Coggle, *Int. J. Radiat. Biol.*, 70(3):351–60, September 1996.
61. Salez et al., *Eur. Respir. J.*, 12(4):913–19, October 1998.
62. Samad et al., *Proc. Natl. Acad. Sci. USA*, 95(13): 7591–96, June 1998.
63. Specks et al., *Am. J. Respir. Crit. Care Med.*, 151(6): 1956–64, June 1995.
64. Stelnicki et al., *Plast. Reconstr. Surg.*, 101(1):12–19, January 1998.
65. Tabibzadeh et al., *Front. Biosci.*, 15(2):a18–25, 1997.
66. Tredget et al., *Plast. Reconstr. Surg.*, 102(5):1317–28, October 1998.
67. Tredget et al., *J. Interferon Cytokine Res.*, 20(2):143–51, February 2000.
68. Ulloa et al., *Nature*, 397:710–13, 1999.
69. Vaillant et al., *Monaldi. Arch. Chest. Dis.*, 51(2):145–52, April 1996.
70. Vossbeck et al., *Int. J. Cancer*, 29;61(1):92–7, March 1995.
71. Weinstein et al., *Cytokine Growth Factor Rev.*, 11(1–2): 49–58, 2000.
72. Wrana et al., *Cell*, 71(6):1003–14, 1992.
73. Wrana et al., *Nature*, 370:341–47, 1994.
74. Yi et al., *Inflammation*, 20(4):339–52, August 1996.
75. Yoshida and Hayashi, *Nippon Rinsho.*, 54(2):418–22, February 1996.
76. Younai et al., *Ann. Plast. Surg.*, 33(2):148–51, August 1994.
77. Zamora et al., *J. Hand. Surg.*, 19(3):435–41, May 1994.
78. Zhang and Jacobberger, *Cell Prolif.*, 29(6):289–307, June 1996.
79. Zhang et al., *J. Invest. Dermatol.*, 104(5):750–54, May 1995.
80. Zhang et al., *Am. J. Pathol.*, 148(2):527–37, February 1996.

All publications mentioned hereinabove are hereby incorporated in their entireties. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for inhibiting activity of TGF-β, comprising bringing tissue expressing TGP-β in direct contact with an amount of an ebaf protein effective to inhibit the activity of TGF-β, wherein the ebaf protein has the amino acid sequence set forth in SEQ ID NO:2.

2. The method of claim 1, wherein the contacting is effected in vivo.

3. The method of claim 2, wherein the contacting is effected in vivo in a mammal.

4. The method of claim 3, wherein the mammal is a human.

5. The method of claim 4, wherein the human has a condition associated with overactivity of TGF-β.

6. The method of claim 5, wherein the condition is fibrosis.

7. The method of claim 6, wherein the fibrosis is a scar, a keloid, cirrhosis, Asherman's syndrome, Meigs' syndrome, a muscular dystrophy, an autoimmune disorder, post-surgical fibrosis, or primary pulmonary fibrosis.

8. The method of claim 7, wherein the scar results from a burn, radiation, a chemical, or a myocardial infarct.

9. The method of claim 7, wherein the muscular dystrophy is Duchenne muscular dystrophy.

10. The method of claim 7, wherein the autoimmune disorder is scleroderma.

11. The method of claim 7, wherein the primary pulmonary fibrosis is Hamman Rich Syndrome or retroperitoneal fibrosis.

12. The method of claim 5, wherein the condition is a defect in cell proliferation.

13. The method of claim 12, wherein the defect in cell proliferation is hyperplasia or neoplasia.

14. The method of claim 5, wherein the condition is a coagulation defect.

15. The method of claim 14, wherein the coagulation defect is menstrual bleeding, abnormal uterine bleeding, coagulopathy, or toxemia of pregnancy.

16. The method of claim 1, wherein the contacting is effected ex vivo.

17. The method of claim 3, wherein the mammal is immunocompromised.

* * * * *